US008216209B2

(12) United States Patent
Consigny et al.

(10) Patent No.: US 8,216,209 B2
(45) Date of Patent: Jul. 10, 2012

(54) METHOD AND APPARATUS FOR DELIVERING AN AGENT TO A KIDNEY

(75) Inventors: Paul M. Consigny, San Jose, CA (US); Fozan O. El-Nounou, Santa Clara, CA (US); David C. Gale, San Jose, CA (US); Pamela A. Kramer-Brown, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 0 days.

(21) Appl. No.: 11/756,376

(22) Filed: May 31, 2007

(65) Prior Publication Data

US 2008/0300573 A1 Dec. 4, 2008

(51) Int. Cl.
*A61M 31/00* (2006.01)
(52) U.S. Cl. .................. 604/509; 604/508
(58) Field of Classification Search .......... 604/509, 604/103.09, 508, 510, 103.01
See application file for complete search history.

(56) References Cited

U.S. PATENT DOCUMENTS

| | | |
|---|---|---|
| 2,701,559 A | 2/1955 | Cooper |
| 3,105,492 A | 10/1963 | Jeckel |
| 3,657,744 A | 4/1972 | Ersek |
| 3,868,956 A | 3/1975 | Alfidi et al. |
| 3,952,747 A | 4/1976 | Kimmell, Jr. |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,171,943 A | 10/1979 | Tschanz et al. |
| 4,323,071 A | 4/1982 | Simpson |
| 4,387,952 A | 6/1983 | Slusher |
| 4,425,908 A | 1/1984 | Simon |
| 4,494,531 A | 1/1985 | Gianturco |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |

(Continued)

FOREIGN PATENT DOCUMENTS

DE 3640745 6/1987

(Continued)

OTHER PUBLICATIONS

Abbott Cardiovascular Systems, Inc. PCT Search Report and Written Opinion mailed Nov. 20, 2008, PCT Appln. No. PCT/US2008/005947, 26 pages.

(Continued)

*Primary Examiner* — Kevin C Sirmons
*Assistant Examiner* — Brandy C Scott
(74) *Attorney, Agent, or Firm* — Randy Shen; Blakely Sokoloff Taylor & Zafman LLP

(57) ABSTRACT

A method is described including introducing a delivery device to a point within a renal artery or a renal segmental artery and delivering a treatment agent from the delivery device according to conditions that create a turbulent blood flow and wherein the treatment agent is capable of inhibiting a biological process contributing to nephropathy. In other embodiments, an apparatus and kit are described including a delivery device for insertion to a point within a renal artery or renal segmental artery and delivery of a treatment agent capable of inhibiting a biological process contributing to nephropathy.

3 Claims, 12 Drawing Sheets

U.S. PATENT DOCUMENTS

| | | |
|---|---|---|
| 4,553,545 A | 11/1985 | Maass et al. |
| 4,560,374 A | 12/1985 | Hammerslag |
| 4,580,568 A | 4/1986 | Gianturco |
| 4,612,931 A | 9/1986 | Dormia |
| 4,616,652 A | 10/1986 | Simpson |
| 4,619,246 A | 10/1986 | Molgaard-Nielsen et al. |
| 4,643,184 A | 2/1987 | Mobin-Uddin |
| 4,649,922 A | 3/1987 | Wiktor |
| 4,650,466 A | 3/1987 | Luther |
| 4,655,771 A | 4/1987 | Wallsten |
| 4,662,885 A | 5/1987 | DiPisa, Jr. |
| 4,665,918 A | 5/1987 | Garza et al. |
| 4,681,110 A | 7/1987 | Wiktor |
| 4,688,553 A | 8/1987 | Metals |
| 4,693,243 A | 9/1987 | Buras |
| 4,706,671 A | 11/1987 | Weinrib |
| 4,723,549 A | 2/1988 | Wholey et al. |
| 4,727,873 A | 3/1988 | Mobin-Uddin |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,781,177 A | 11/1988 | Lebigot |
| 4,790,812 A | 12/1988 | Hawkins, Jr. et al. |
| 4,790,813 A | 12/1988 | Kensey |
| 4,793,348 A | 12/1988 | Palmaz |
| 4,794,928 A | 1/1989 | Kletschka |
| 4,795,458 A | 1/1989 | Regan |
| 4,800,882 A | 1/1989 | Gianturco |
| 4,830,003 A | 5/1989 | Wolff et al. |
| 4,832,055 A | 5/1989 | Palestrant |
| 4,848,343 A | 7/1989 | Wallsten et al. |
| 4,856,516 A | 8/1989 | Hillstead |
| 4,870,966 A | 10/1989 | Dellon et al. |
| 4,873,978 A | 10/1989 | Ginsburg |
| 4,877,030 A | 10/1989 | Beck et al. |
| 4,878,906 A | 11/1989 | Lindemann et al. |
| 4,886,061 A | 12/1989 | Fischell et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,478 A | 5/1990 | Solano et al. |
| 4,921,479 A | 5/1990 | Grayzel |
| 4,921,484 A | 5/1990 | Hillstead |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,969,891 A | 11/1990 | Gewertz |
| 4,986,831 A | 1/1991 | King et al. |
| 4,988,356 A | 1/1991 | Crittenden et al. |
| 4,990,155 A | 2/1991 | Wilkoff |
| 4,990,156 A | 2/1991 | Lefebvre |
| 4,994,071 A | 2/1991 | MacGregor |
| 4,997,435 A | 3/1991 | Demeter |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,053,008 A | 10/1991 | Bajaj |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,428 A | 11/1991 | Cope et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,839 A | 3/1992 | Kipperman |
| 5,092,877 A | 3/1992 | Pinchuk |
| 5,100,423 A | 3/1992 | Fearnot |
| 5,100,425 A | 3/1992 | Fischell et al. |
| 5,100,429 A | 3/1992 | Sinofsky et al. |
| 5,102,415 A | 4/1992 | Guenther et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,108,419 A | 4/1992 | Reger et al. |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,133,733 A | 7/1992 | Rasmussen et al. |
| 5,135,536 A | 8/1992 | Hillstead |
| 5,152,777 A | 10/1992 | Goldberg et al. |
| 5,158,548 A | 10/1992 | Lau et al. |
| 5,160,342 A | 11/1992 | Reger et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,286 A | 3/1993 | Phan et al. |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,207,644 A | 5/1993 | Strecker |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,256,146 A | 10/1993 | Ensminger et al. |
| 5,279,565 A | 1/1994 | Klein et al. |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,120 A | 4/1994 | Crandell et al. |
| 5,304,200 A | 4/1994 | Spaulding |
| 5,306,250 A | 4/1994 | March et al. |
| 5,314,444 A | 5/1994 | Gianturco |
| 5,314,472 A | 5/1994 | Fontaine |
| 5,324,304 A | 6/1994 | Rasmussen |
| 5,329,942 A | 7/1994 | Gunther et al. |
| 5,330,482 A | 7/1994 | Gibbs et al. |
| 5,330,500 A | 7/1994 | Song |
| 5,336,178 A | 8/1994 | Kaplan et al. |
| 5,344,426 A | 9/1994 | Lau et al. |
| 5,350,398 A | 9/1994 | Pavcnik et al. |
| 5,354,279 A | 10/1994 | Hofling |
| 5,354,308 A | 10/1994 | Simon et al. |

| Patent No. | Date | Inventor |
|---|---|---|
| 5,356,433 A | 10/1994 | Rowland et al. |
| 5,360,401 A | 11/1994 | Turnland et al. |
| 5,368,566 A | 11/1994 | Crocker |
| 5,370,657 A | 12/1994 | Irie |
| 5,372,600 A | 12/1994 | Beyar et al. |
| 5,375,612 A | 12/1994 | Cottenceau et al. |
| 5,378,239 A | 1/1995 | Termin et al. |
| 5,383,887 A | 1/1995 | Nadal |
| 5,383,892 A | 1/1995 | Cardon et al. |
| 5,405,378 A | 4/1995 | Strecker |
| 5,415,637 A | 5/1995 | Khosravi |
| 5,419,777 A | 5/1995 | Hofling |
| 5,421,832 A | 6/1995 | Lefebvre |
| 5,421,955 A | 6/1995 | Lau et al. |
| 5,423,745 A | 6/1995 | Todd et al. |
| 5,423,885 A | 6/1995 | Williams |
| 5,445,646 A | 8/1995 | Euteneuer et al. |
| 5,449,373 A | 9/1995 | Pinchasik et al. |
| 5,456,667 A | 10/1995 | Ham et al. |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,507,768 A | 4/1996 | Lau et al. |
| 5,514,154 A | 5/1996 | Lau et al. |
| 5,545,132 A | 8/1996 | Fagan et al. |
| 5,549,626 A | 8/1996 | Miller et al. |
| 5,571,135 A | 11/1996 | Fraser et al. |
| 5,601,595 A | 2/1997 | Smith |
| 5,603,721 A | 2/1997 | Lau et al. |
| 5,609,574 A | 3/1997 | Kaplan et al. |
| 5,611,775 A | 3/1997 | Machold et al. |
| 5,626,604 A | 5/1997 | Cottone, Jr. |
| 5,626,605 A | 5/1997 | Irie et al. |
| 5,634,942 A | 6/1997 | Chevillon et al. |
| 5,639,274 A | 6/1997 | Fischell et al. |
| 5,649,953 A | 7/1997 | Lefebvre |
| 5,653,690 A | 8/1997 | Booth et al. |
| 5,653,691 A | 8/1997 | Rupp et al. |
| 5,653,727 A | 8/1997 | Wiktor |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,693,029 A | 12/1997 | Leonhardt |
| 5,695,518 A | 12/1997 | Laerum |
| 5,695,519 A | 12/1997 | Summers et al. |
| 5,713,860 A | 2/1998 | Kaplan et al. |
| 5,713,863 A | 2/1998 | Vigil et al. |
| 5,716,396 A | 2/1998 | Williams, Jr. |
| 5,720,726 A | 2/1998 | Marcadis et al. |
| 5,720,764 A | 2/1998 | Naderlinger |
| 5,725,550 A | 3/1998 | Nadal |
| 5,733,294 A | 3/1998 | Forber et al. |
| 5,733,303 A | 3/1998 | Israel et al. |
| 5,733,325 A | 3/1998 | Robinson et al. |
| 5,735,893 A | 4/1998 | Lau et al. |
| 5,746,767 A | 5/1998 | Smith |
| 5,755,781 A | 5/1998 | Jayaraman |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,782,855 A | 7/1998 | Lau et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,521 A | 9/1998 | Orth |
| 5,800,525 A | 9/1998 | Bachinski et al. |
| 5,810,871 A | 9/1998 | Tuckey et al. |
| 5,810,874 A | 9/1998 | Lefebvre |
| 5,814,064 A | 9/1998 | Daniel et al. |
| 5,817,152 A | 10/1998 | Birdsall et al. |
| 5,827,324 A | 10/1998 | Cassell et al. |
| 5,830,217 A | 11/1998 | Ryan |
| 5,833,650 A | 11/1998 | Imran |
| 5,836,868 A | 11/1998 | Ressemann et al. |
| 5,836,965 A | 11/1998 | Jendersee et al. |
| 5,846,251 A | 12/1998 | Hart |
| 5,846,260 A | 12/1998 | Maahs |
| 5,848,964 A | 12/1998 | Samuels |
| 5,851,210 A | 12/1998 | Torossian |
| 5,855,600 A | 1/1999 | Alt |
| 5,868,708 A | 2/1999 | Hart et al. |
| 5,873,852 A | 2/1999 | Vigil et al. |
| 5,876,367 A | 3/1999 | Kaganov et al. |
| 5,876,374 A | 3/1999 | Alba et al. |
| 5,882,335 A | 3/1999 | Leone et al. |
| 5,891,108 A | 4/1999 | Leone et al. |
| 5,893,852 A | 4/1999 | Morales |
| 5,897,567 A | 4/1999 | Ressemann et al. |
| 5,902,332 A | 5/1999 | Schatz |
| 5,904,670 A | 5/1999 | Schreiner |
| 5,910,154 A | 6/1999 | Tsugita et al. |
| 5,911,734 A | 6/1999 | Tsugita et al. |
| 5,921,944 A | 7/1999 | Borodulin et al. |
| 5,924,997 A | 7/1999 | Campbell |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,951,599 A | 9/1999 | McCrory |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,984,964 A | 11/1999 | Roberts et al. |
| 5,989,281 A | 11/1999 | Barbut et al. |
| 5,997,468 A | 12/1999 | Wolff et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,030,413 A | 2/2000 | Lazarus |
| 6,042,598 A | 3/2000 | Tsugita et al. |
| 6,048,484 A | 4/2000 | House et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,066,168 A | 5/2000 | Lau et al. |
| 6,068,622 A | 5/2000 | Sater et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,102,904 A | 8/2000 | Vigil et al. |
| 6,117,101 A | 9/2000 | Diederich et al. |
| 6,117,154 A | 9/2000 | Barbut et al. |
| 6,129,739 A | 10/2000 | Khosravi |
| 6,129,754 A | 10/2000 | Kanesaka et al. |
| 6,136,015 A | 10/2000 | Kurz et al. |
| 6,136,016 A | 10/2000 | Barbut et al. |
| 6,142,987 A | 11/2000 | Tsugita |
| 6,146,358 A | 11/2000 | Rowe |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |

| | | |
|---|---|---|
| 6,187,025 B1 | 2/2001 | Machek |
| 6,190,405 B1 | 2/2001 | Culombo et al. |
| 6,203,561 B1 | 3/2001 | Ramee et al. |
| 6,206,868 B1 | 3/2001 | Parodi |
| 6,210,392 B1 | 4/2001 | Vigil et al. |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,026 B1 | 6/2001 | Campbell et al. |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan et al. |
| 6,270,513 B1 | 8/2001 | Tsugita et al. |
| 6,273,901 B1 | 8/2001 | Whitcher et al. |
| 6,273,910 B1 | 8/2001 | Limon |
| 6,273,913 B1 | 8/2001 | Wright et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,280,414 B1 | 8/2001 | Shah et al. |
| 6,280,451 B1 | 8/2001 | Bates et al. |
| 6,283,947 B1 | 9/2001 | Mirzaee |
| 6,287,321 B1 | 9/2001 | Jang |
| 6,287,336 B1 | 9/2001 | Globerman et al. |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,325,826 B1 | 12/2001 | Vardi et al. |
| 6,334,871 B1 | 1/2002 | Dor et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,358,247 B1 | 3/2002 | Altman et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,402,778 B2 | 6/2002 | Wang |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,440,162 B1 | 8/2002 | Cox et al. |
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,971 B1 | 9/2002 | Andrus et al. |
| 6,450,989 B2 | 9/2002 | Dubrul et al. |
| 6,451,044 B1 | 9/2002 | Naghavi et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,178 B1 | 11/2002 | Andrews et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,862 B1 | 12/2002 | Ray et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin et al. |
| 6,565,591 B2 | 5/2003 | Brady et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,577,895 B1 | 6/2003 | Altman |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,569 B2 * | 7/2003 | Bigus et al. .................. 604/523 |
| 6,592,606 B1 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,226 B1 | 8/2003 | Smith et al. |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |

| | | |
|---|---|---|
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B1 | 11/2003 | Gilson et al. |
| 6,652,480 B1 | 11/2003 | Imran et al. |
| 6,652,505 B1 | 11/2003 | Tsugita |
| 6,652,554 B1 | 11/2003 | Wholey et al. |
| 6,652,557 B1 | 11/2003 | MacDonald |
| 6,652,579 B1 | 11/2003 | Cox et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,663,880 B1 | 12/2003 | Roorda et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,648 B2 | 2/2004 | Flaherty et al. |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,830 B2 | 2/2004 | Vigil et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boylan et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson et al. |
| 6,726,702 B2 | 4/2004 | Khosravi |
| 6,726,703 B2 | 4/2004 | Broome et al. |
| 6,733,474 B2 | 5/2004 | Kusleika et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,749,598 B1 | 6/2004 | Keren et al. |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle et al. |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison et al. |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan et al. |
| 6,902,540 B2 | 6/2005 | Dorros et al. |
| 6,905,476 B2 | 6/2005 | Ponzi |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews et al. |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah et al. |
| 6,964,672 B2 | 11/2005 | Brady et al. |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo et al. |
| 6,979,344 B2 | 12/2005 | Jones et al. |
| 6,986,778 B2 | 1/2006 | Zadno-Azizi |
| 6,989,019 B2 | 1/2006 | Mazzocchi et al. |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,903 B2 | 2/2006 | Wijay et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey et al. |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |

| | | |
|---|---|---|
| 7,044,958 B2 | 5/2006 | Douk et al. |
| 7,048,752 B2 | 5/2006 | Mazzocchi et al. |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland et al. |
| 7,094,249 B1 | 8/2006 | Broome et al. |
| 7,097,440 B2 | 8/2006 | Papp et al. |
| 7,097,651 B2 | 8/2006 | Harrison et al. |
| 7,097,834 B1 | 8/2006 | Boyle |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 7,217,255 B2 | 5/2007 | Boyle et al. |
| 7,241,304 B2 | 7/2007 | Boyle et al. |
| 2001/0000799 A1 | 5/2001 | Wessman et al. |
| 2001/0007059 A1 | 7/2001 | Mirzaee |
| 2001/0010014 A1 | 7/2001 | Trozera |
| 2001/0012951 A1 | 8/2001 | Bates et al. |
| 2001/0032011 A1 | 10/2001 | Stanford |
| 2001/0047138 A1 | 11/2001 | Kokate et al. |
| 2002/0009535 A1 | 1/2002 | Michal et al. |
| 2002/0062147 A1 | 5/2002 | Yang |
| 2002/0077564 A1 | 6/2002 | Campbell et al. |
| 2002/0082515 A1 | 6/2002 | Campbell et al. |
| 2002/0091408 A1 | 7/2002 | Sutton et al. |
| 2002/0091409 A1 | 7/2002 | Sutton et al. |
| 2002/0091436 A1 | 7/2002 | Phelps et al. |
| 2002/0095141 A1 | 7/2002 | Belef et al. |
| 2002/0099406 A1 | 7/2002 | St. Germain |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0107561 A1 | 8/2002 | Pinheiro |
| 2002/0111648 A1 | 8/2002 | Kusleika et al. |
| 2002/0111659 A1 | 8/2002 | Davis et al. |
| 2002/0115942 A1 | 8/2002 | Stanford et al. |
| 2002/0120286 A1 | 8/2002 | DoBrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0128706 A1 | 9/2002 | Osypka |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0151959 A1 | 10/2002 | Von Oepen |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165574 A1* | 11/2002 | Ressemann et al. .......... 606/194 |
| 2002/0165576 A1 | 11/2002 | Boyle et al. |
| 2002/0169413 A1 | 11/2002 | Keren et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0183763 A1 | 12/2002 | Callol et al. |
| 2002/0188313 A1 | 12/2002 | Johnson et al. |
| 2002/0188314 A1 | 12/2002 | Anderson et al. |
| 2002/0193825 A1 | 12/2002 | McGuckin, Jr. et al. |
| 2002/0193826 A1 | 12/2002 | McGuckin, Jr. et al. |
| 2002/0193827 A1 | 12/2002 | McGuckin, Jr. et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady |
| 2003/0040772 A1 | 2/2003 | Hyodoh et al. |
| 2003/0042186 A1 | 3/2003 | Boyle |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0105515 A1 | 6/2003 | Skubitz et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0114921 A1 | 6/2003 | Yoon |
| 2003/0120303 A1 | 6/2003 | Boyle et al. |
| 2003/0125802 A1 | 7/2003 | Callol et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0181973 A1 | 9/2003 | Sahota |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |

| | | | | | | |
|---|---|---|---|---|---|---|
| 2003/0208228 A1 | 11/2003 | Gilson et al. | | 2004/0193208 A1 | 9/2004 | Talpade et al. |
| 2003/0208229 A1 | 11/2003 | Kletschka | | 2004/0199198 A1 | 10/2004 | Beulke et al. |
| 2003/0212361 A1 | 11/2003 | Boyle et al. | | 2004/0199199 A1 | 10/2004 | Krolik et al. |
| 2003/0212429 A1 | 11/2003 | Keegan et al. | | 2004/0199203 A1 | 10/2004 | Oslund et al. |
| 2003/0212431 A1 | 11/2003 | Brady et al. | | 2004/0204737 A1 | 10/2004 | Boismier et al. |
| 2003/0212434 A1 | 11/2003 | Thielen | | 2004/0210250 A1 | 10/2004 | Eskuri |
| 2003/0216774 A1 | 11/2003 | Larson | | 2004/0214772 A1* | 10/2004 | Quay et al. ................... 514/12 |
| 2003/0220665 A1 | 11/2003 | Eskuri et al. | | 2004/0220608 A1 | 11/2004 | D'Aquanni et al. |
| 2003/0225418 A1 | 12/2003 | Eskuri et al. | | 2004/0220609 A1 | 11/2004 | Douk et al. |
| 2003/0225435 A1 | 12/2003 | Huter et al. | | 2004/0220611 A1 | 11/2004 | Ogle |
| 2003/0229295 A1 | 12/2003 | Houde et al. | | 2004/0225322 A1 | 11/2004 | Garrison et al. |
| 2003/0229374 A1 | 12/2003 | Brady et al. | | 2004/0230156 A1 | 11/2004 | Schreck et al. |
| 2003/0233117 A1 | 12/2003 | Adams et al. | | 2004/0236368 A1 | 11/2004 | McGucklin, Jr. et al. |
| 2003/0236545 A1 | 12/2003 | Gilson | | 2004/0236369 A1 | 11/2004 | Dubrul |
| 2004/0002730 A1 | 1/2004 | Denison et al. | | 2004/0249409 A1 | 12/2004 | Krolik et al. |
| 2004/0006361 A1 | 1/2004 | Boyle et al. | | 2004/0254601 A1 | 12/2004 | Eskuri |
| 2004/0006364 A1 | 1/2004 | Ladd | | 2004/0254602 A1 | 12/2004 | Lehe et al. |
| 2004/0006365 A1 | 1/2004 | Brady et al. | | 2004/0260308 A1 | 12/2004 | Gilson et al. |
| 2004/0006366 A1 | 1/2004 | Huter et al. | | 2004/0260333 A1 | 12/2004 | Dubrul et al. |
| 2004/0006367 A1 | 1/2004 | Johnson et al. | | 2004/0267301 A1 | 12/2004 | Boylan et al. |
| 2004/0006368 A1 | 1/2004 | Mazzocchi et al. | | 2004/0267302 A1 | 12/2004 | Gilson et al. |
| 2004/0015184 A1 | 1/2004 | Boyle et al. | | 2004/0267353 A1 | 12/2004 | Gregorich |
| 2004/0019363 A1 | 1/2004 | Hanson et al. | | 2005/0004594 A1 | 1/2005 | Nool et al. |
| 2004/0024445 A1 | 2/2004 | Dickson | | 2005/0004595 A1 | 1/2005 | Boyle et al. |
| 2004/0034385 A1 | 2/2004 | Gilson et al. | | 2005/0004597 A1 | 1/2005 | McGuckin, Jr. et al. |
| 2004/0039411 A1 | 2/2004 | Gilson et al. | | 2005/0010245 A1 | 1/2005 | Wasicek |
| 2004/0044359 A1 | 3/2004 | Renati et al. | | 2005/0010246 A1 | 1/2005 | Streeter et al. |
| 2004/0044360 A1 | 3/2004 | Lowe | | 2005/0010247 A1 | 1/2005 | Kusleika et al. |
| 2004/0044400 A1 | 3/2004 | Cheng et al. | | 2005/0021075 A1 | 1/2005 | Bonnette et al. |
| 2004/0049226 A1 | 3/2004 | Keegan et al. | | 2005/0021076 A1 | 1/2005 | Mazzocchi et al. |
| 2004/0059179 A1* | 3/2004 | Maguire et al. ............. 600/16 | | 2005/0055048 A1 | 3/2005 | Dieck et al. |
| 2004/0059372 A1 | 3/2004 | Tsugita | | 2005/0070953 A1 | 3/2005 | Riley |
| 2004/0059373 A1 | 3/2004 | Shapiro et al. | | 2005/0070991 A1 | 3/2005 | Pienknagura |
| 2004/0064091 A1 | 4/2004 | Keren et al. | | 2005/0075663 A1 | 4/2005 | Boyle et al. |
| 2004/0064099 A1 | 4/2004 | Chiu | | 2005/0080446 A1 | 4/2005 | Gilson et al. |
| 2004/0082967 A1 | 4/2004 | Broome et al. | | 2005/0085842 A1 | 4/2005 | Eversull et al. |
| 2004/0082968 A1 | 4/2004 | Krolik et al. | | 2005/0090845 A1 | 4/2005 | Boyd |
| 2004/0086550 A1 | 5/2004 | Roorda et al. | | 2005/0090857 A1 | 4/2005 | Kusleika |
| 2004/0088000 A1 | 5/2004 | Muller | | 2005/0090858 A1 | 4/2005 | Pavlovic |
| 2004/0088002 A1 | 5/2004 | Boyle et al. | | 2005/0090888 A1 | 4/2005 | Hines et al. |
| 2004/0093009 A1 | 5/2004 | Denison et al. | | 2005/0096691 A1 | 5/2005 | Groothuis et al. |
| 2004/0093010 A1 | 5/2004 | Gesswein et al. | | 2005/0096692 A1 | 5/2005 | Linder et al. |
| 2004/0093011 A1 | 5/2004 | Vrba | | 2005/0101986 A1 | 5/2005 | Daniel et al. |
| 2004/0093012 A1 | 5/2004 | Cully et al. | | 2005/0101987 A1 | 5/2005 | Salahieh |
| 2004/0093013 A1 | 5/2004 | Brady et al. | | 2005/0101988 A1 | 5/2005 | Stanford et al. |
| 2004/0097900 A1* | 5/2004 | Keren et al. ............. 604/500 | | 2005/0101989 A1 | 5/2005 | Cully et al. |
| 2004/0098022 A1 | 5/2004 | Barone | | 2005/0113865 A1 | 5/2005 | Daniel et al. |
| 2004/0098026 A1 | 5/2004 | Joergensen et al. | | 2005/0119688 A1 | 6/2005 | Bergheim |
| 2004/0098032 A1 | 5/2004 | Papp et al. | | 2005/0119689 A1 | 6/2005 | Mazzocchi et al. |
| 2004/0098033 A1 | 5/2004 | Leeflang et al. | | 2005/0119690 A1 | 6/2005 | Mazzocchi et al. |
| 2004/0102807 A1 | 5/2004 | Kusleika et al. | | 2005/0119691 A1 | 6/2005 | Daniel et al. |
| 2004/0102831 A1 | 5/2004 | Murray, III | | 2005/0124931 A1 | 6/2005 | Fulton et al. |
| 2004/0106944 A1 | 6/2004 | Daniel et al. | | 2005/0125023 A1 | 6/2005 | Bates et al. |
| 2004/0111111 A1 | 6/2004 | Lin | | 2005/0131450 A1 | 6/2005 | Nicholson et al. |
| 2004/0116960 A1 | 6/2004 | Demond et al. | | 2005/0131453 A1 | 6/2005 | Parodi |
| 2004/0122466 A1 | 6/2004 | Bales | | 2005/0149110 A1 | 7/2005 | Wholey et al. |
| 2004/0127933 A1 | 7/2004 | Demond et al. | | 2005/0149112 A1 | 7/2005 | Barbut |
| 2004/0127934 A1 | 7/2004 | Gilson et al. | | 2005/0149113 A1 | 7/2005 | Douk et al. |
| 2004/0127936 A1 | 7/2004 | Salahieh et al. | | 2005/0159772 A1 | 7/2005 | Lowe et al. |
| 2004/0138693 A1 | 7/2004 | Eskuri et al. | | 2005/0159773 A1 | 7/2005 | Broome et al. |
| 2004/0138694 A1 | 7/2004 | Tran et al. | | 2005/0159774 A1 | 7/2005 | Belef |
| 2004/0138696 A1 | 7/2004 | Drasler et al. | | 2005/0171573 A1 | 8/2005 | Salahieh et al. |
| 2004/0147939 A1 | 7/2004 | Rabkin et al. | | 2005/0177187 A1 | 8/2005 | Gray et al. |
| 2004/0147955 A1 | 7/2004 | Beulke et al. | | 2005/0182440 A1 | 8/2005 | Bates et al. |
| 2004/0153118 A1 | 8/2004 | Clubb et al. | | 2005/0182441 A1 | 8/2005 | Denison et al. |
| 2004/0153119 A1 | 8/2004 | Kusleika et al. | | 2005/0192623 A1 | 9/2005 | Mazzocchi et al. |
| 2004/0158275 A1 | 8/2004 | Crank et al. | | 2005/0192624 A1 | 9/2005 | Mazzocchi et al. |
| 2004/0158277 A1 | 8/2004 | Lowe et al. | | 2005/0203567 A1 | 9/2005 | Linder et al. |
| 2004/0158278 A1 | 8/2004 | Becker et al. | | 2005/0203568 A1 | 9/2005 | Burg et al. |
| 2004/0158279 A1 | 8/2004 | Petersen | | 2005/0203569 A1 | 9/2005 | Kusleika et al. |
| 2004/0158280 A1 | 8/2004 | Morris et al. | | 2005/0203570 A1 | 9/2005 | Mazzocchi et al. |
| 2004/0158281 A1 | 8/2004 | Boylan et al. | | 2005/0203571 A1 | 9/2005 | Mazzocchi et al. |
| 2004/0167564 A1 | 8/2004 | Fedie | | 2005/0209634 A1 | 9/2005 | Brady et al. |
| 2004/0167565 A1 | 8/2004 | Beulke et al. | | 2005/0209635 A1 | 9/2005 | Gilson et al. |
| 2004/0167566 A1 | 8/2004 | Beulke et al. | | 2005/0216051 A1 | 9/2005 | Mazzocchi et al. |
| 2004/0167567 A1 | 8/2004 | Cano et al. | | 2005/0216052 A1 | 9/2005 | Mazzocchi et al. |
| 2004/0167568 A1 | 8/2004 | Boylan et al. | | 2005/0216053 A1 | 9/2005 | Douk et al. |
| 2004/0172055 A1 | 9/2004 | Huter et al. | | 2005/0222583 A1 | 10/2005 | Cano et al. |
| 2004/0176794 A1 | 9/2004 | Khosravi | | 2005/0222604 A1 | 10/2005 | Schaeffer |

| | | | | | | |
|---|---|---|---|---|---|---|
| 2005/0222607 | A1 | 10/2005 | Palmer et al. | EP | 0428479 | 5/1991 |
| 2005/0228437 | A1 | 10/2005 | Gilson et al. | EP | 0472334 | 2/1992 |
| 2005/0228438 | A1 | 10/2005 | Sachar et al. | EP | 0517075 | 12/1992 |
| 2005/0228439 | A1 | 10/2005 | Andrews et al. | EP | 0533511 | 3/1993 |
| 2005/0234502 | A1 | 10/2005 | Gilson et al. | EP | 0540290 | 5/1993 |
| 2005/0240141 | A1 | 10/2005 | Aliski et al. | EP | 0541443 | 5/1993 |
| 2005/0240215 | A1 | 10/2005 | Ellis | EP | 0807424 | 11/1997 |
| 2005/0245866 | A1 | 11/2005 | Azizi | EP | 1127556 | 8/2001 |
| 2005/0245882 | A1 | 11/2005 | Elkins et al. | EP | 1588731 | 10/2005 |
| 2005/0267517 | A1 | 12/2005 | Ungs | FR | 2580504 | 10/1986 |
| 2005/0283184 | A1 | 12/2005 | Gilson et al. | FR | 2677872 | 12/1992 |
| 2005/0283185 | A1 | 12/2005 | Linder et al. | GB | 2020557 | 11/1979 |
| 2005/0283186 | A1 | 12/2005 | Berrada et al. | GB | 2070490 | 9/1981 |
| 2005/0288632 | A1 | 12/2005 | Willard | GB | 2135585 | 11/1983 |
| 2005/0288705 | A1 | 12/2005 | Gilson et al. | JP | 58501458 | 9/1983 |
| 2006/0004403 | A1 | 1/2006 | Gilson et al. | JP | 62213762 | 9/1987 |
| 2006/0004405 | A1 | 1/2006 | Salahieh et al. | JP | 62231657 | 10/1987 |
| 2006/0015138 | A1 | 1/2006 | Gertner | JP | 62235496 | 10/1987 |
| 2006/0015139 | A1 | 1/2006 | Tsugita et al. | JP | 63214264 | 9/1988 |
| 2006/0015141 | A1 | 1/2006 | Linder et al. | JP | 1083685 | 3/1989 |
| 2006/0020285 | A1 | 1/2006 | Niermann | JP | 1299550 | 12/1989 |
| 2006/0020286 | A1 | 1/2006 | Niermann | JP | 2174859 | 7/1990 |
| 2006/0025803 | A1 | 2/2006 | Mitelberg et al. | JP | 2255157 | 10/1990 |
| 2006/0025804 | A1 | 2/2006 | Krolik et al. | JP | 3009745 | 1/1991 |
| 2006/0025805 | A1 | 2/2006 | DoBrava et al. | JP | 3009746 | 1/1991 |
| 2006/0030814 | A1* | 2/2006 | Valencia et al. ........... 604/93.01 | JP | 3057465 | 3/1991 |
| 2006/0030876 | A1 | 2/2006 | Peacock, III et al. | JP | 3151983 | 6/1991 |
| 2006/0030877 | A1 | 2/2006 | Martinez et al. | JP | 4025755 | 1/1992 |
| 2006/0030878 | A1 | 2/2006 | Anderson et al. | JP | 63246178 | 10/1998 |
| 2006/0052817 | A1 | 3/2006 | Russo et al. | WO | WO-89/01798 | 3/1989 |
| 2006/0074446 | A1 | 4/2006 | Gilson et al. | WO | WO-89/08433 | 9/1989 |
| 2006/0079859 | A1* | 4/2006 | Elkins et al. .................. 604/508 | WO | WO-91/07139 | 5/1991 |
| 2006/0095069 | A1 | 5/2006 | Shah et al. | WO | WO-92/03097 | 3/1992 |
| 2006/0100659 | A1 | 5/2006 | Dinh et al. | WO | WO-92/06734 | 4/1992 |
| 2006/0100662 | A1 | 5/2006 | Daniel et al. | WO | WO-92/09246 | 6/1992 |
| 2006/0100663 | A1 | 5/2006 | Palmer et al. | WO | WO-96/01591 | 1/1996 |
| 2006/0106366 | A1* | 5/2006 | Wang ............................ 604/509 | WO | WO-96/40325 | 12/1996 |
| 2006/0116715 | A1 | 6/2006 | Khosravi et al. | WO | WO-97/17100 | 5/1997 |
| 2006/0122643 | A1 | 6/2006 | Wasicek | WO | WO-97/42998 | 11/1997 |
| 2006/0122644 | A1 | 6/2006 | Brady et al. | WO | WO-98/02084 | 1/1998 |
| 2006/0122645 | A1 | 6/2006 | Brady et al. | WO | WO-98/33443 | 8/1998 |
| 2006/0129181 | A1 | 6/2006 | Callol et al. | WO | WO-99/16382 | 4/1999 |
| 2006/0129182 | A1 | 6/2006 | Gilson et al. | WO | WO-99/22673 | 5/1999 |
| 2006/0129183 | A1 | 6/2006 | Boyle et al. | WO | WO-99/23976 | 5/1999 |
| 2006/0149312 | A1 | 7/2006 | Arguello et al. | WO | WO-99/44510 | 9/1999 |
| 2006/0149313 | A1 | 7/2006 | Arguello et al. | WO | WO-99/44542 | 9/1999 |
| 2006/0149314 | A1 | 7/2006 | Borillo et al. | WO | WO-99/66970 | 12/1999 |
| 2006/0155322 | A1 | 7/2006 | Sater et al. | WO | WO-00/67667 | 11/2000 |
| 2006/0161198 | A1 | 7/2006 | Sakai et al. | WO | WO-00/67670 | 11/2000 |
| 2006/0167491 | A1 | 7/2006 | Wholey et al. | WO | WO-00/67825 | 11/2000 |
| 2006/0184194 | A1 | 8/2006 | Pal et al. | WO | WO-01/10346 | 2/2001 |
| 2006/0189960 | A1 | 8/2006 | Kesten et al. | WO | WO-01/41861 | 6/2001 |
| 2006/0190025 | A1 | 8/2006 | Lehe et al. | WO | WO-01/45592 | 6/2001 |
| 2006/0195137 | A1 | 8/2006 | Sepetka et al. | WO | WO-01/49215 | 7/2001 |
| 2006/0195138 | A1 | 8/2006 | Goll et al. | WO | WO-01/82835 | 11/2001 |
| 2006/0200047 | A1 | 9/2006 | Galdonik et al. | WO | WO-01/87183 | 11/2001 |
| 2006/0200191 | A1 | 9/2006 | Zadno-Azizi | WO | WO 03/002028 | 1/2003 |
| 2006/0206139 | A1 | 9/2006 | Tekulve | WO | WO-03/068306 | 8/2003 |
| 2006/0224234 | A1 | 10/2006 | Jayaraman | | | |
| 2006/0265043 | A1 | 11/2006 | Mandrusov et al. | | | |
| 2007/0067009 | A1 | 3/2007 | Gandhi et al. | | | |
| 2007/0129752 | A1 | 6/2007 | Webler et al. | | | |
| 2007/0250035 | A1 | 10/2007 | El-Nounou et al. | | | |

FOREIGN PATENT DOCUMENTS

| | | |
|---|---|---|
| DE | 3823060 | 1/1989 |
| DE | 19605864 | 8/1996 |
| EP | 0062300 | 10/1982 |
| EP | 0221570 | 5/1987 |
| EP | 0338816 | 10/1989 |
| EP | 0361192 | 4/1990 |
| EP | 0364787 | 4/1990 |
| EP | 0372789 | 6/1990 |
| EP | 0380668 | 8/1990 |
| EP | 0407951 | 1/1991 |
| EP | 0408245 | 1/1991 |
| EP | 0421729 | 4/1991 |
| EP | 0423916 | 4/1991 |
| EP | 0427429 | 5/1991 |

OTHER PUBLICATIONS

Chowdhury, Ibrul, et al., "Regulation of Connective Tissue Growth Factor (CTGF/CCN2) Gene Transcription and mRNA Stability in Smooth Muscle Cells," Eur. J. Biochem. 271, 2004, pp. 4436-4450.
Lloberas, Nuria, et al., "Mammalian Target of Rapamycin Pathway Blockade Slows Progression of Diabetic Kidney Disease in Rats," Journal of the American Society of Nephrology 17, 2006, pp. 1395-1404.
"70th Scientific Assembly and Annual Meeting: Scientific Program," Radiology, Special Edition, vol. 153(P), Washington, D.C., Nov. 1984, pp. 206.
"71st Scientific Assembly and Annual Meeting: Scientific Program," Radiology, Special Edition, vol. 153(P), Washington, D.C., Nov. 1985, pp. 66.
"72nd Scientific Assembly and Annual Meeting: RSNA Scientific Program," Radiology, Special Edition, vol. 161(P), Chicago, IL, Nov. 1986, pp. 40.
"PE Plus Peripheral Balloon Dilation Catheter," C.R. Bard, Inc., USCI Division, Aug. 1985.

Bonzel, T. et al., "The Sliding Rail System (Monorail): Description of a New Technique for Intravascular Instrumentation and Its Application to Coronary Angioplasty," Kardiologie, Supplemental 6, 1987, pp. 119-122.

Charnsangavej, D. et al., "Endovascular Stent for Use in Aortic Dissection: An In Vitro Experiment," Radiology, Nov. 1985, pp. 323-324, 157(2).

Charnsangavej, Chusilp et al., "Stenosis of the Vena Cava: Preliminary Assessment of Treatment with Expandable Metallic Stents," Radiology, Nov. 1986, pp. 295-298, 161.

Cragg, et al., "Non-Surgical Placement of Arterial Endoprostheses: A New Technique Using Nitinol Wire," Radiology Journal, Apr. 1983, pp. 261-263.

Dotter, Charles T., "Transluminal Expandable Nitinol Coil Stent Grafting: Preliminary Report," Radiology Journal, Apr. 1983, pp. 259-260.

Dotter, Charles T., "Transluminally Placed Coilspring Endarterial Tube Grafts," Investigative Radiology, Sep./Oct. 1969, pp. 329-332.

Duprat, et al., "Flexible Balloon-Expanded Stent for Small Vessels," Radiology Journal, 1985, pp. 73-77.

Finci, Leo et al., "Percutaneous Transluminal Coronary Angioplasty of a Bifurcation Narrowing Using the Kssing Wire Monorail Balloon Technique," The American Journal of Cardiology, Aug. 1987, pp. 375-376, 60.

Furui, Shigeru et al., "Hepatic Inferior Vena Cava Obstruction: Treatment of Two Types with Gianturco Expandable Metallic Stents," Radiology, Sep. 1990, pp. 665-670.

Garasic, Joseph M., et al., "Stent and Artery Geometry Determine Intimal Thickening Independent of Arterial Injury," Circulation, Feb. 2000, pp. 812-818.

Harrington, J.D. et al., "The Palmaz-Schatz Stent," Handbook of Cardiovascular Interventions/Vascular Interventions, pp. 563-572.

Kubler, M. et al., "Zeitschrift fur Kardiologie," Abstracts, German Journal of Cardiology, Band 80, Supplementum 3, Apr. 1991, pp. 28-29.

Lawrence, David D., Jr. et al., "Percutaneous Endovascular Graft: Experimental Evaluation," Radiology, May 1987, pp. 357-360, 163.

Lee, Jeong et al., "Stent deployable at a low pressure and a stent delivery system," U.S. Appl. No. 10/802,435, filed Mar. 16, 2004.

Maass, et al., "Radiological Follow-Up of Transluminally Inserted Vascular Endoprosthese: An Experimental Study Using Expanding Spirals," Radiology Journal, 1984, pp. 659-663.

Mirich, et al., "Percutaneously Placed Endovascular Grafts for Aoertic Aneurysms: Feasibility Study," Radiology, Part 2, 1989, pp. 1033-1037.

Palmaz, et al., "Expandable Intraluminal Graft: A Preliminary Study," Raiodiology Journal, 1985, pp. 73-77.

PCT Search Report and Written Opinion for PCT/US2007/009418, mailed Oct. 4, 2007, 17 pages.

Rosch, Josef et al., "Experimental Intrahepatic Portacaval Anastomosis: Use of Expandable Gianturco Stents," Radiology, Feb. 1987, pp. 481-485, 162.

Rosch, Josef et al., "Gianturco Expandable Stents in Experimental and Clinical Use," Twelfth Annual Course of Diagnostic Angiography and Interventional Radiology (Pittsburgh, PA), Mar. 1987, pp. 121-124.

Rosch, Josef et al., "Gianturco Expandable Wire Stents in the Treatment of Superior Vena Cava Syndrome Recurring after Maximum-Tolerance Radiation," Cancer, Sep. 1987, pp. 1243-1246, 60.

Rosch, Josef et al., "Modified Gianturco Expandable Wire Stents in Experimental and Clinical Use," Annales de Radiologie, 1988, pp. 100-103, 31(2).

Rosch, Jr., M.D. et al., "Transjugular Intrahepatic Portacaval Shunt: An Experimental Work," The American Journal of Surgery, May 1971, pp. 588-592, 121.

Strupp, G. et al., "Clinical and Angiographic Short and Medium Term Results after Coronary Stenting," Zeitschrift fur Kardiologie, 1992, pp. 500-506, 81.

Van Der Geissen, Willem J., et al., "Coronary Stenting with a new, Radiopaque Balloon-Expandable Endoprosthesis in Pigs," Circulation, May 1991, pp. 93-149, 83(5).

Wallace, Michael J., et al., "Tracheobronchia Tree: Expandable Metallic Stents Used in Experimental and Clinical Applications (Work in Progress)," Radiology, Feb. 1986, pp. 309-312, 158.

Wright, et al., "Percutaneous Endovascular Stents: An Experimental Evaluation," Radiology Journal, 1985, pp. 69-72.

Yoshioka, et al., "Development and Clinical Application of Biliary Endoprosthesis Using Expandable Metallic Stents," Japan Radiological Society, 1988, pp. 1183-1185, 48(9).

Yoshioka, et al., "Self-Expanding Endovascular Graft: An Experimental Study in Dogs," American Journal of Roentgeriology, Oct. 1988, pp. 673-676, 151.

Zeltinger, J. et al., "Advances in the Development of Coronary Stents," Biomaterials Forum, 2004, pp. 8-9, 24.

Abbott Cardiovascular Systems, Inc., PCT Invitation to Pay Additional Fees and Partial Search Report mailed Aug. 27, 2008, PCT Application No. PCT/US2008/005947, 9 pages.

Abbott Cardiovascular Systems, International Preliminary Report on Patentability dated Dec. 10, 2009 for PCT/US2008/005947.

Abbott Cardiovascular Systems, Final office action dated Jun. 2, 2010 for U.S. Appl. No. 10/802,435,.

* cited by examiner

METHOD AND APPARATUS FOR DELIVERING AN AGENT TO A KIDNEY

FIELD

Delivery systems for delivery of a treatment agent to a kidney for inhibiting nephropathy or end-stage renal disease.

BACKGROUND

Nephropathy is a disease that typically develops over a prolonged period (e.g., 10-15 years) during which time the ability of the kidneys to properly function diminishes. Once the disease has progressed to end-stage renal disease (ESRD), a kidney transplant or dialysis may be the only treatment option. The disease is caused, for example, by immune disorders (e.g. IgA nephropathy) or diabetes (e.g. diabetic nephropathy). In either case, nephropathy is characterized by the trapping of protein deposits, such as, the protein immunoglobulin A (IgA), inside glomerular capillaries of the kidney. These glomerular capillaries serve as the kidney's filtration system to filter waste and water from the blood. The protein deposits prevent the glomerular capillaries from properly filtering the blood resulting in high protein levels in the urine.

Once the glomerular capillaries are damaged, they cannot be repaired. Thus, treatment of nephropathy typically involves slowing the progression of the disease rather than curing it. Treatment may consist of, for example, administration of therapeutics, such as angiotensin converting enzyme (ACE) inhibitors which reduce urine protein levels. A solution of the therapeutic may be delivered to the kidneys systemically. Systemic delivery, however, has several disadvantages. In particular, in systemic delivery techniques, the whole organism is treated therefore greater amounts of drugs must be supplied which are sometimes toxic to the organism.

Local delivery techniques may be used to overcome some of the disadvantages of systemic delivery techniques, however, a separate set of problems arise. Typically, in local delivery techniques the therapeutic is injected into a blood stream at a point upstream from the treatment site or into an unperfused vessel region after first occluding the vessel region to inhibit blood flow. In either case, due to the natural laminar flow profiles within the renal artery and kidney and reduced blood flow to diseased kidney regions, the blood flow may not evenly distribute the therapeutic to the desired treatment site.

SUMMARY

According to an embodiment, methods and apparatus for delivery of a treatment agent to a kidney for inhibiting nephropathy or end-stage renal disease are described. Representatively, in one embodiment, a method includes introducing a delivery device to a point within a renal system. The point may be within a renal artery, a renal segmental artery or a renal cortex. The delivery device may include, but is not limited to, a catheter assembly or a stent implant. A treatment agent may be delivered from the delivery device to a treatment site according to conditions that create a turbulent blood flow to facilitate even distribution of the treatment agent at the treatment site. By distributing the treatment agent to the kidney in this manner, the beneficial effects of the treatment agent are maximized at a desired treatment site within the renal system. Delivery of the treatment agent according to conditions that create a turbulent blood flow may include, delivering a treatment agent to a lumen modified to alter a blood flow or injecting a treatment agent into a blood flow in a direction perpendicular to the direction of flow such that a typical laminar flow profile of the blood is altered. Additionally, in one embodiment, delivery further comprises delivering the treatment agent according to conditions that prevent back flow of the treatment agent into, for example, an aorta. In this aspect, a balloon or sheath of the delivery device may be expanded in a vessel region upstream from a point of treatment agent delivery. Alternatively, backflow may be prevented by releasing the treatment agent from a delivery port of the delivery device at a flow rate less than a natural flow rate of the artery. The treatment agent may include a property to inhibit a biological process contributing to nephropathy. Such biological processes may include, but are not limited to, changes in glomerular basement membrane, changes in mesangial matrix deposition and podocyte apoptosis.

In another embodiment, an apparatus is described. Representatively, the apparatus includes a primary cannula having dimensions suitable for insertion into a renal artery and/or a branch thereof such as a renal segmental artery. The primary cannula may include a first end, a second end and a medial portion along a length of the catheter body between the first end and the second end. An aperture may be positioned within the medial portion of the primary cannula such that when the apparatus is positioned within the renal artery the first end is within the renal artery and the aperture is within an aorta. The first end may include a first port and a second port. The first port is in fluid communication with the aperture and both the first port and the aperture are dimensioned to divert blood flowing from an aorta to the renal artery into the aperture and out of the first port. The first end may include a second port that may be adapted for advancing a guidewire therethrough.

According to another embodiment, an apparatus is described that may include a balloon expandable intralumenal framework to create a turbulent flow within a vessel. Representatively, the apparatus may include a balloon expandable intralumenal framework comprising a first end and a second end defining a length dimension less than a length of a renal artery. The framework may include axially-oriented anchor portions along the length dimension capable of anchoring to a vessel lumen. The anchor portions may be wound around a distal end of a primary cannula such that blood may flow through a channel winding around the primary cannula to alter a speed of the blood flow and provide a turbulent flow. The apparatus may further include an inflation cannula for expanding a balloon of the framework and a delivery cannula for delivering a treatment agent within the turbulent flow. In this aspect, the apparatus facilitates mixing and even distribution of the treatment agent throughout the kidney.

According to another embodiment, an apparatus is described having a dilating balloon assembly including pores along a portion of a balloon of the balloon assembly to modify the flow of blood within a vessel lumen and a direction of flow of a treatment agent released from a delivery cannula of the apparatus. The apparatus includes a guidewire cannula having dimensions for insertion into a renal artery and/or a renal segmental artery. A dilatable balloon assembly is connected to the guidewire cannula having a balloon including a distal taper wall. The distal taper wall consists of pores along only a region of the distal taper wall defined by a diameter of a lumen of the artery. The apparatus further includes a delivery cannula having an end within the balloon for dilating the balloon assembly and delivering a treatment agent such that the treatment agent is released into the vessel lumen through the pores.

In still further embodiments, an apparatus is described having a sheath extending from an end of a catheter body to provide a turbulent flow within a vessel and reduce backflow of a treatment agent delivered from the apparatus. The apparatus may include a primary cannula having dimensions for insertion into a renal artery and a lumen dimensioned for inserting a delivery cannula having a sheath extending from an end of the delivery cannula therethrough. The sheath may include an outer diameter substantially equivalent to an inner diameter of a renal artery to retain a same perimeter of the inner diameter of the renal artery when the sheath is deployed. The sheath may be of a material that allows blood flow to a region of the renal artery distal to the sheath to create a turbulent blood flow.

In one embodiment, another apparatus is described including an implant for delivery of a treatment agent. Representatively, in one embodiment the implant may be an intravascular stent implant. The stent implant includes a plurality of struts connected together by a plurality of links. The intravascular stent implant may be dimensioned to be deployed in a renal artery. Alternatively, the intravascular stent implant may be dimensioned to be deployed in a segmental artery. The implant may include a treatment agent for delivery to a kidney. The treatment agent may have a property to inhibit a biological process contributing to nephropathy.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION

Figure 1:
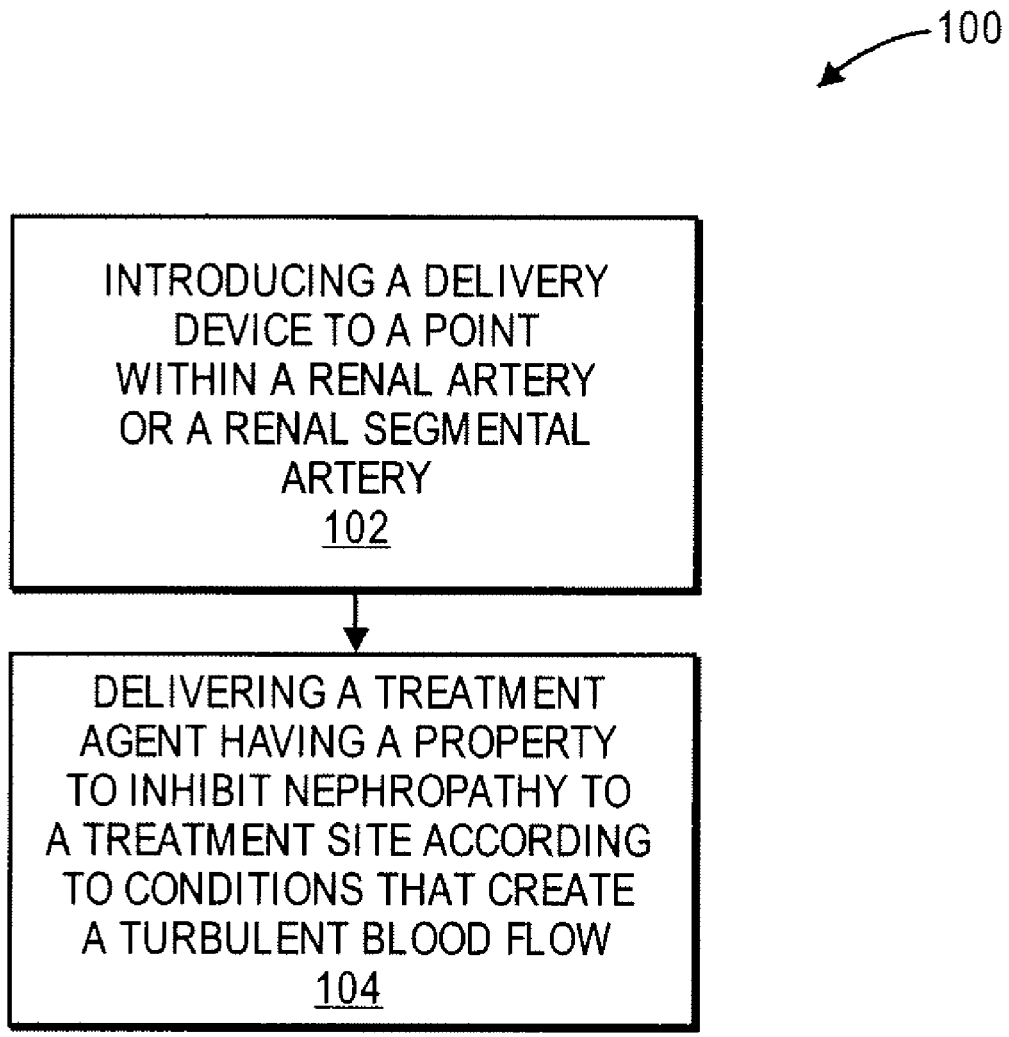
FIG. 1 illustrates a flow chart of a method for delivering a treatment agent to a kidney.

FIG. 1 shows a flow chart of a method for delivering a treatment agent to a kidney. In one embodiment, the method includes introducing a delivery device to a point within a renal artery or a renal segmental artery that supplies the renal cortex (block 102). Alternatively, the point may be within a renal cortex of a kidney. The delivery device is intended to broadly include any medical device for insertion into a physiological lumen to permit injection and/or withdrawal of fluids of varying viscosities to maintain patency of a lumen of a blood vessel or an area defining the lumen, or for other purposes. The delivery device may further include any medical device for insertion into a physiological lumen capable of releasing a treatment agent. The point to which the delivery device is introduced may be a treatment site or a region adjacent to a treatment site. The treatment site may be a diseased region within a renal vessel or other tissue of a kidney.

In one embodiment, the treatment agent is delivered according to conditions that create a turbulent blood flow within a region of treatment agent delivery (block 104). The term "turbulent blood flow" as used herein generally refers to a flow profile characterized by a chaotic or agitated blood flow or otherwise modified flow profile which may include rapid variations of pressure, flow direction and/or velocity. For example, in some embodiments, turbulent blood flow is created in a vessel lumen by partially occluding the vessel lumen by about 60 percent (%) to about 95%. Typically, the flow profile of blood flowing through the renal artery to the kidney is laminar, meaning the fluid flows in parallel layers, or streams, with little or no disruption between the layers. This profile continues along the kidney opening, or hilum, and into the segmental arteries leading to the glomerular capillaries within the renal cortex. Thus, when the treatment agent is released from a single point of a delivery device into one of these streams of a healthy kidney most, if not all, of the treatment agent is carried only to the kidney region at the end of the stream. In this aspect, only a small portion of the kidney receives the treatment agent. Moreover, blood flow to the diseased regions especially in need of the treatment agent may be reduced or stop all together as a result of the disease. In such cases, even where the treatment agent is released into a path normally destined for the diseased region, it will not reach the desired treatment region. Such problems may be overcome where turbulence is created within the flow profile and the treatment agent is dispersed into the turbulent blood flow. In particular, the turbulent conditions will facilitate mixing of the treatment agent with the blood and disrupt the pathways typically found within the kidney so that the treatment agent is more evenly distributed throughout the kidney.

In one aspect, conditions creating a turbulent blood flow may include partially occluding a region of the artery lumen so as to provide a constricted pathway for blood flow (e.g., about 60% to about 95% lumen occlusion). The narrowed pathway causes the speed of the blood flowing through the narrower region to increase resulting in turbulent blood flow. The treatment agent may then be injected into the turbulent blood flow. Turbulent blood flow may further be created within a lumen of a delivery device. In this aspect, a fluid, such as a saline or blood, may be delivered through the lumen of the device and a treatment agent may be injected into the flowing fluid. In other embodiments, the conditions creating a turbulent blood flow may include injecting a treatment agent within a vessel lumen in a direction perpendicular to the direction of blood flow. In this aspect, the normal direction of blood flow is altered by the stream of treatment agent bisecting the normal flow path resulting in a turbulent flow. Due to the turbulence, the treatment agent is homogenously distributed throughout the blood for delivery to the treatment site. In addition, the turbulence may disrupt the downstream laminar flow profiles within the kidney. The homogenous distribution of the treatment agent throughout blood flowing to the kidney and disruption of flow profiles within the kidney facilitate an even distribution of the treatment agent solution throughout the kidney tissues.

Delivery of the treatment agent to the treatment site may further be maximized by preventing backflow of the treatment agent. The term "backflow" as used herein generally refers to a flow of treatment agent in a direction opposite to that in which it is desired to be delivered. For example, in some cases the treatment site is unable to retain the full volume of treatment agent being delivered. In this aspect, the extra volume of treatment agent is rejected and, where delivery is within the renal artery, flows into the adjacent aorta (i.e. backflow). In one embodiment, such backflow may be prevented by partially or fully occluding a vessel region upstream from the treatment site before delivering the treatment agent. Blocking may be accomplished, by expanding, for example, a balloon or a sheath of the delivery device within the vessel. The balloon or sheath essentially serves as a backstop to any unabsorbed treatment agent delivered to the treatment site that may begin to flow toward the balloon or sheath. Alternatively, backflow may be prevented by releasing the treatment agent from a delivery port of the delivery device at a flow rate less than a natural flow rate of the artery. For example, it is estimated that a flow rate of blood through the renal artery to the kidney is about 500 milliliters per minute (ml/min), thus in order to prevent backflow, the treatment agent may be delivered within the renal artery at a flow rate less than about 500 ml/min.

Figure 2:
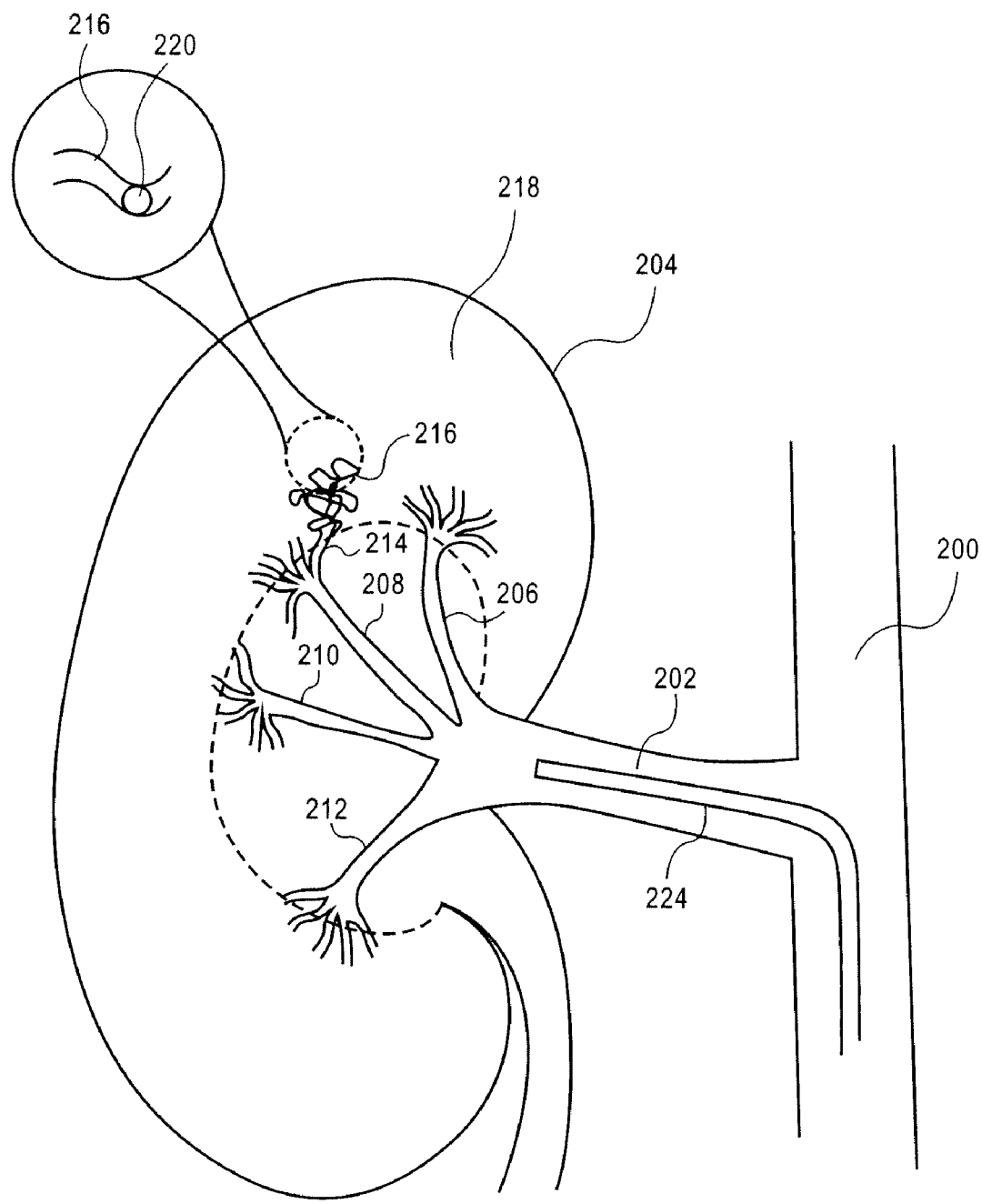
FIG. 2 shows a cross-sectional side view of a kidney and a method for delivering a treatment agent to the kidney.

In other embodiments, delivery of an effective amount of the treatment agent to the treatment site may be maximized by altering a particle size of the treatment agent. As illustrated in FIG. 2, a lower branch of aorta 200 feeds blood to kidney 204 through renal artery 202. Renal artery 202 branches off into renal segmental arteries 206, 208, 210 and 212 and arterioles 214. Each arteriole 214 in turn leads to a tuft of capillaries 216, also known as a glomerulus. Blood from segmental arteries 206, 208, 210 and 212 flows into the glomerulus at the end of each segmental artery 206, 208, 210 and 212 where it is filtered to remove fluid and solutes from the blood. In one embodiment, as illustrated in FIG. 2, a distal end of delivery device 224 may be positioned at a point within renal artery 202. Alternatively, delivery device 224 may be positioned at a point within renal segmental arteries 206, 208, 210 and 212. A proximal portion of delivery device 224 remains outside of the body to facilitate loading of the treatment agent within delivery device 224. Representatively, a femoral artery may be punctured and delivery device 224 may be advanced through the femoral artery, to aorta 200 and then into renal artery 202. Alternatively, delivery device 224 may be advanced through a brachial artery, down aorta 200 and into renal artery 202. In still further embodiments, an external iliac artery may be punctured and delivery device 224 may be advanced through the external iliac artery to a common iliac artery, to aorta 200 and then into renal artery 202.

It is further contemplated that delivery device 224 may be introduced to a point within kidney 204 via a retroperitoneal insertion technique. In this aspect, a distal end of delivery device 224 may be inserted through a back of a patient adjacent kidney 204. Delivery device 224 may then be advanced through a surface of kidney 204 to a point within renal cortex 218 adjacent to glomerulus 216. In this aspect, when the treatment agent is delivered via delivery device 224, the treatment agent is localized to an area proximal to glomerular capillaries within the kidney to facilitate treatment of the kidney. Alternatively, delivery device 224 may be introduced through a back region of the patient and into renal artery 202. In this embodiment, the treatment agent may then be delivered by delivery device 224 through renal artery 202 to a desired treatment site.

In an embodiment illustrated in FIG. 2, a treatment agent loaded within delivery device 224 may be released into, for example, renal artery 202 such that the treatment agent flows through segmental artery 208 and into glomerulus 216. In one embodiment, the treatment agent may be loaded into a carrier having a large enough diameter such that the carrier becomes lodged within a narrow lumen of a capillary within the glomerulus 216. This aspect is shown in the exploded view of glomerulus 216 of FIG. 2. In this embodiment, treatment agent 220 flows into glomerulus 216 and becomes lodged within the lumen. For example, in some embodiments the treatment agent may have a diameter from about 8 microns to about 15 microns. Thus, release of the treatment agent from within the carrier is localized to glomerulus 216. Thus, delivery of the treatment agent may be confined to a specific treatment site within the kidney.

Treatment Agents

As used herein, treatment agents are intended to include, but are not limited to, drugs, biologically active agents, chemically active agents, therapeutic agents, and the like, and pharmaceutical compositions thereof, which can be used to deliver a treatment agent to a treatment site within a kidney as described herein. The treatment agents are delivered alone or in combination to the treatment site.

In one embodiment, the treatment agent may include a property to inhibit a biological process contributing to nephropathy. Such biological processes may include, but are not limited to, changes in glomerular basement membrane, changes in mesangial matrix deposition and podocyte attachment and/or apoptosis.

In one embodiment, the treatment agent may include a drug. The drug may have a property to inhibit undesirable effects of the renin-angiotensin system in the kidneys. The renin-angiotensin system responds to a decrease in the perfusion of the juxtaglomerular apparatus found in afferent arterioles of the glomerulus of the kidney by constricting glomerular arterioles. Such constriction causes blood to build up in the glomerulus and increase glomerular pressure. Representative drugs that may act to inhibit this process include, but are not limited to, angiotensin converting enzyme (ACE) inhibitors, angiotensin receptor blockers (ARBs) and renin inhibitors.

In still further embodiments, the treatment agent may include a drug to inhibit protein kinase C. Representative drugs may include, but are not limited to, ruboxistaurin (LY333531), enzastaurin (LY317615), bisindolylmaleimide IX, chelerythrine, edelfosine, edelfosina, ET18OCH3, H-7, HA-100, H89, HA-1004, Ro 31-8220, rottlerin, staurosporine and quercetin.

The transforming growth factor-beta system contributes to the progression of renal damage due to stimulation of extracellular matrix deposition. Thus, in further embodiments, the treatment agent may include an agent having a property to inhibit transforming growth factor beta, its receptor and SMAD and other signaling molecules downstream of the receptor. Representative inhibitors may include, but are not limited to antisense molecules, ribozymes, siRNA, antibodies, receptor kinase inhibitors and other small molecule inhibitors such as halofuginone, sirolimus, everolimus, biolimus ABT578 and nuclear receptor agonists such as estradiol, retinoids, and peroxisome proliferator-activated receptors (PAR) agonists.

It is further recognized that connective tissue growth factor (CTGF) is present in glomeruli in patients with diabetic nephropathy. CTGF is a member of the centrosomin (CCN) family of proteins, which regulate biological processes including stimulation of cell proliferation, migration, and adhesion. It is believed that expression of CTGF in diabetic kidneys contributes to the development of glomerulosclerosis by affecting matrix synthesis and its turnover. In this aspect, the treatment agent may include an agent having a property to inhibit connective tissue growth factor. Representative agents having a property to inhibit connective tissue growth factor may include, but are not limited to antibodies, interleukin-1 (IL-1) alpha and beta, Rho A GTPase inhibitors, and p38 MAP kinase inhibitors.

In some embodiments, the treatment agent may be modified to enhance uptake of the agent into the desired tissue. In this aspect, the treatment agent may be delivered to the desired tissue in a formulation which may include vasoactive agents as enhancers of vascular permeability called excipients, such as thrombin, bradykinin and histamine. These excipients have properties which increase endothelial porosity and thereby enhance uptake of the treatment agent into the tissue.

The treatment agent may be delivered in a form including, but not limited to, a solution. For example, in some embodiments, a desired amount of treatment agent is mixed with saline or an iodine free-contrast media to form the solution.

In some embodiments, the treatment agent may be delivered to the desired tissue in a carrier. In one aspect, the carrier may be a sustained-release carrier which allows for controlled release of the treatment agent over time at the desired treatment site. "Carrier" includes a matrix that contains one or more treatment agents. A suitable carrier may take the form of a nanoparticle (e.g., nanosphere), microparticle (e.g., microsphere) or liposome as the situation may dictate. The carrier with the treatment agent encapsulated inside may be incorporated into a solution including an oily solution for delivery to the desired tissue.

The carrier may be a bioerodable carrier (hereinafter interchangeably referred to as sustained-release carriers) infused with a treatment agent. Suitable materials for sustained-release carriers include, but are not limited to, encapsulation polymers such as poly(L-lactide), poly(D,L-lactide), poly(glycolide), poly(lactide-co-glycolide), polycaprolactone, polyanhydride, polydiaxanone, polyorthoester, polyamino acids, or poly(trimethylene carbonate), and combinations thereof.

Treatment agents, including treatment agents combined with a carrier (e.g., a sustained release carrier), having a size greater than about 10 microns have the potential, when introduced into the renal artery, of being trapped in the glomerular capillaries. In this aspect, the treatment agent may be released over time at a point within the glomerular capillaries. In other embodiments, the carrier size may be between about 1 micron to 100 microns, still further between about 8 microns to about 15 microns and in some embodiments between about 1 micron to 2 microns. In other embodiments, the carrier size may be between about 10 microns and 14 microns. In still further embodiments where the treatment agent is delivered at a point outside of a vessel lumen, such as the kidney cortex, the treatment agent or a carrier encapsulating the treatment agent may be any size capable of being delivered through a lumen of the delivery device, such as for example, a size as small as one nanometer (nm) to as large as about 100 microns.

Various methods may be employed to formulate and infuse the carrier with one or more treatment agents. The embodiments of the composition of infused carrier may be prepared by conventional methods where all components are combined then blended. In some embodiments, carriers may be prepared using a predetermined amount of a polymer or a pre-polymer that is added to a predetermined amount of a solvent or a combination of solvents. The solvent is mutually compatible with the polymer and is capable of placing the polymer into solution at the concentration desired in the solution. Examples of solvents may include, but are not limited to, dimethylsulfoxide (DMSO), Dimethyl Acetamide (DMAC), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

By way of example, and not limitation, the polymer may comprise from about 0.1% to about 35%, more narrowly about 2% to about 20% by weight of the total weight of the total solution, and the solvent may comprise from about 65% to about 99.9%, more narrowly about 80% to about 98% by weight, of the total weight of the total solution. A specific weight ratio is dependent on factors such as the material from which the delivery device is made and the geometrical structure of the device.

Sufficient amounts of treatment agent are dispersed or dissolved in the carrier. The amount of treatment agent introduced into the carrier may be any amount sufficient to inhibit a biological process contributing to nephropathy when released within the renal system. The treatment agent may be in solution or suspension. If the treatment agent is not completely soluble in the composition, operations including mixing, stirring, and/or agitation may be employed to effect homogeneity. The treatment agent may be added so that the dispersion is in fine particles. The mixing of the treatment agent may be conducted in an anhydrous atmosphere, at ambient pressure and at room temperature.

In some embodiments using microparticles and/or nanoparticles, the microparticles and/or nanoparticles may be sustained release carriers prepared by a water/oil/water (W/O/W) double emulsion method. The W1 phase, an aqueous phase containing treatment agent, is dispersed into the oil phase consisting of polymer dissolved in organic solvent (e.g., dichloromethane) using a high-speed homogenizer. Examples of sustained-release polymers that may be used include, but are not limited to, poly(D,L-lactide-co-glycolide) (PLGA), poly(D,L-lactide) (PLA) or PLA-PEEP copolymers, poly-ester-amide co-polymers (PEA) and polyphophazines. The primary water-in-oil (W/O) emulsion is then dispersed to an aqueous solution containing a polymeric surfactant, e.g., poly(vinyl alcohol) (PVA), and further homogenized to produce a W/O/W emulsion. After stirring for several hours, the microparticles and/or nanoparticles are collected by filtration.

In some embodiments, the sustained-release carrier is a liposome. "Liposomes" are artificial vesicles that are approximately spherical in shape and can be produced from natural phospholipids and cholesterol. In one method, phospholipids are mixed with cholesterol in chloroform. Suitable phospholipids include, but are not limited to, dimyristoyl phosphatidyl choline or dipalmitoyl phosphatidyl ethanolamine. In some embodiments, a hydrophobic treatment agent may be added with an optional co-solvent. After mixing, the solvent (and optional co-solvent) may be evaporated with heat or ambient temperature in a round bottom flask. Resultant lipids may be deposited on the glass surface. In some embodiments, a hydrophilic treatment agent and water may be added to the flask and sonicated to form liposomes. The resultant solution may be pressure filtered through ceramic pore size controlled filters to reduce liposome particle size. In still further embodiments, the carrier is a microbubble formed by any technique deemed desirable.

In some embodiments, a surface of the carrier may be modified to enhance affinity of the encapsulated treatment agent to tissue lining the walls of the glomerular capillaries. In this aspect, the surface may be coated with binding agents. The binding agent may include a protein or small molecule that will facilitate retention of the carrier and encapsulated treatment agent at the treatment site so as to induce and/or modulate a therapeutic response through interaction with a specific binding site (e.g., a receptor within a cell or on a cell surface). Representative binding agents and their associated receptors include, but are not limited to, CD11b/CD18 (MAC-1) or aL/beta2 integrin (LFA-1) and intracellular adhesion molecule-1 (ICAM-1) receptor, integrin avb3 which binds to RGD-containing peptide and E-selectin which binds to Sialyl-Lewis glycoprotein.

A surface charge of the carrier may further be modified (e.g. positively, negatively or neutral) to accommodate and enhance binding characteristics to the glomerular tissue. The endothelial cells and basement membrane along the normal glomerular capillary walls are typically electronegatively charged. As diseases such as glomerulosclerosis and diabetic nephropathy progresses, however, these cells slowly lose the electronegative charge. It is believed that modifying the carriers to have an electropositive charge will enhance binding of the carrier and encapsulated agent within the capillary. In this aspect, a carrier encapsulating the treatment agent may be modified by any standard method suitable for providing the carrier surface with an electropositive charge. In one embodiment, positively charged carriers may be made by coating carriers with Chitosan. Alternatively, positively charged carriers may be made, for example, entirely of Chitosan in a water-in-oil emulsion process and crosslinked with glutaraldehye or genipin. In this aspect, the treatment agent may be swell loaded in the crosslinked spheres. Still further, if the treatment agent is soluble at pH 5, the treatment agent may be incorporated into the initial Chitosan solution, provided it does not subsequently react with the aldehyde crosslinker. Another approach for forming cationic carriers may include using a poly-lysine graft of PLGA.

In still further embodiments, a surface of the carrier may be coated with active agents or other species to enhance the range of functionalities of the product. For example, the surface may be coated with a monoclonal antibody that selectively binds to proteins expressed within the glomerulus (glomerular endothelium, basement membrane, podocytes) and tubules (tubular epithelium and basement membrane). A representative example is the monoclonal antibody anti CD90/Thy 1 that binds to OX-7 a glomerular basement membrane protein. Other proteins to target include nephrin and podocin.

Delivery Devices

Figure 3:
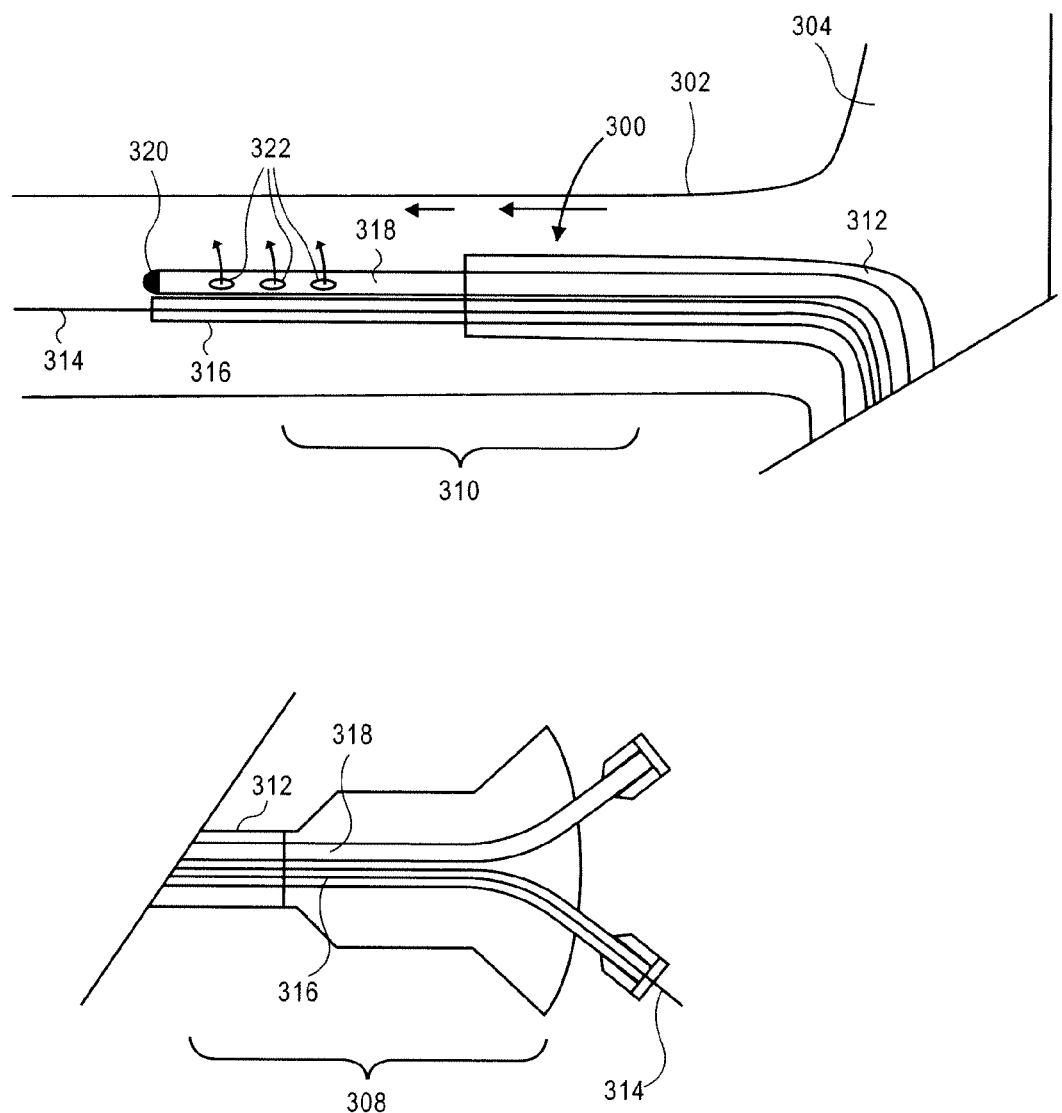
FIG. 3 shows a cross-sectional side view of a blood vessel of a renal region and one embodiment of a delivery system to deliver a treatment agent to a kidney.

FIG. 3 shows blood vessels of a renal region and one embodiment of a delivery system to deliver a treatment agent to a kidney. FIG. 3 shows a renal artery 302 extending from aorta 304 and having a delivery device 300 disposed therein. Delivery device 300 includes a proximal portion 308 and a distal portion 310. Proximal portion 308 may be external to renal artery 302 and to the patient. Representatively, delivery device 300 may be inserted through a femoral artery and through, for example, a guide catheter and with the aid of a guidewire 314 to a location in a renal artery or renal segmental artery of a patient. Alternatively, delivery device 300 may be introduced to the point within the renal system of the patient by inserting delivery device 300 through a region of the patient's back adjacent a kidney and then advancing delivery device 300 into the kidney renal cortex or a renal artery. FIG. 3 shows distal portion 310 of delivery device 300 positioned at a point within renal artery 302. Alternatively, delivery device 300 may be positioned at a point within a renal segmental artery or a renal cortex.

In one embodiment, delivery device 300 includes a primary cannula 312 having a length that extends from proximal portion 308 (e.g. located external to a patient during a procedure) to distal portion 310. Primary cannula 312 has a lumen therethrough sized to accommodate a guidewire cannula 316 and a delivery cannula 318. It is contemplated that primary cannula 312 may be a single lumen catheter as illustrated in FIG. 3 or, in some embodiments, a dual lumen catheter. In some embodiments where delivery device 300 is introduced to a location within a renal artery, guidewire cannula 316 and delivery cannula 318 may have a width of about 5 French to about 7 French (3 French=1 mm). In other embodiments where delivery device 300 is introduced to a location within a renal segmental artery, guidewire cannula 316 and delivery cannula 318 may have a width of about 2 French to about 4 French.

Delivery cannula 318 may extend from proximal portion 308 of delivery device 300 to distal portion 310. Delivery cannula 318 may have a distal end that is occluded 320. Holes 322 are disposed along a length of the distal end so that the treatment agent is emitted from holes 322 in a direction perpendicular to the direction of blood flow. Delivery of the treatment agent perpendicular to the direction of blood flow, in addition to the narrowing of the vessel lumen due to device 300, disrupts the blood flow thereby creating turbulent conditions. The turbulence facilitates mixing of the treatment agent into the blood flow and even distribution of the treatment agent at the desired treatment site, for example, distal to deliver device 300. Additionally, emitting the treatment agent out of the sides of the device in this manner does not increase a flow rate of fluid (e.g. mixture of blood and treatment agent) delivered to the treatment site therefore backflow from the delivery of the mixture of blood and treatment agent into the treatment site is minimized.

Guidewire cannula 316 has a lumen sized to accommodate a guidewire 314. Delivery device 300 may be an over the wire (OTW) configuration wherein guidewire cannula 316 extends from a proximal end (e.g., external to a patient during a procedure) to a distal end of delivery device 300. Guidewire cannula 316 may also be used for delivery of a treatment agent such as an agent having a property to inhibit nephropathy or a formulation including vasoactive agents which enhance binding characteristics to glomeruli of the kidney when guidewire 314 is removed with delivery device 300 in place. In such case, separate delivery cannula (i.e., delivery cannula 318) is unnecessary. Alternatively, delivery cannula 318 may be used to deliver one treatment agent while guidewire cannula 316 is used to deliver another treatment agent.

In another embodiment, catheter assembly 300 is a rapid-exchange-type (RX-type) delivery device and only a portion of catheter assembly 300 (e.g., a distal portion 310) is advanced over guidewire 314. In a RX-type of delivery device, typically, the guidewire cannula extends from the distal end of the delivery device to the proximal guidewire port which is typically spaced a substantial distance from the proximal end of the delivery device.

Figure 4:
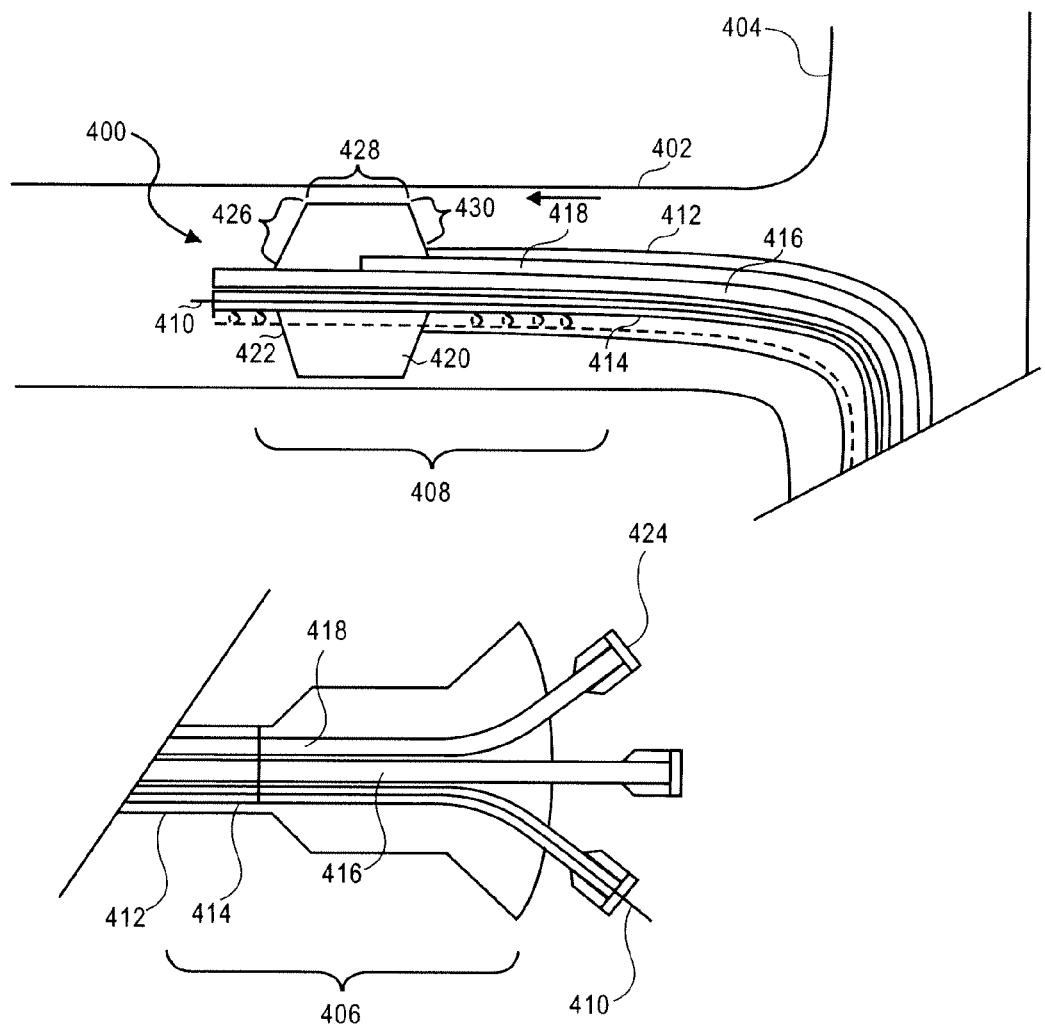
FIG. 4 shows a cross-sectional side view of a blood vessel of a renal region and another embodiment of a delivery system to deliver a treatment agent to a kidney.

FIG. 4 shows a blood vessel of a renal region and another embodiment of a delivery system to deliver a treatment agent to a kidney. FIG. 4 shows a renal artery 402 branching off of aorta 404 and having a delivery device 400 disposed therein. Delivery device 400 includes a proximal portion 406 and a distal portion 408. Proximal portion 406 may be external to renal artery 402 and to the patient. Representatively, delivery device 400 may be inserted through a femoral artery and through, for example, a guide catheter and with the aid of a guidewire 410 to a location in a renal artery or renal segmental artery of a patient. FIG. 4 shows distal portion 408 of delivery device 400 positioned at a point within renal artery 402. Alternatively, delivery device 400 may be positioned at a point within a renal segmental artery.

In one embodiment, delivery device 400 includes a primary cannula 412 having a length that extends from proximal portion 406 (e.g. located external to a patient during a procedure) to connect with a proximal end or skirt of a balloon 420. Primary cannula 412 has a lumen therethrough that includes a guidewire cannula 414, a delivery cannula 416 and an inflation cannula 418. Delivery cannula 416 may extend from proximal portion 406 of delivery device 400 to distal portion 408. Inflation cannula 418 further extends from proximal portion 406 of delivery device 400 to distal portion 408. Inflation cannula 418 has a distal end that terminates within balloon 420. In one embodiment, catheter assembly 400 is introduced into renal artery 402 and balloon 420 is inflated via inflation cannula 418.

Primary cannula 412, as well as those described in reference to other embodiments, may be a polymer material that may include markers to allow the cannula to be identified using fluoroscopic or angiographic techniques. For example, a metal band (e.g., stainless steel, platinum, or tungsten loaded polymer) that may be detected by fluoroscopic or angiographic techniques.

Balloon 420 is connected to a distal end of delivery device 400 and is in fluid communication with inflation cannula 418. Balloon 420 includes balloon wall or membrane 422 which is selectively inflatable to dilate from a collapsed configuration to a desired and controlled expanded configuration. Balloon 420 can be selectively expanded by supplying a fluid into inflation cannula 418 at a predetermined rate of pressure through a delivery port 424. Balloon wall 422 is selectively deflatable, after inflation, to return to the collapsed configuration or a deflated profile. In one embodiment, balloon wall 422 can be defined by three sections, distal taper wall 426, medial working length 428, and proximal taper wall 430. In one embodiment, proximal taper wall 430 can taper at any suitable angle θ, typically between about 10° to less than about 90°, when balloon 420 is in the expanded configuration.

Distal taper wall 426, medial working length 428, and proximal taper wall 430 of balloon wall 422 can be bound together by seams or be blown out of a single seamless material. Balloon 420 can be made from any suitable material, including, but not limited to, polymers and copolymers of polyolefins, polyamides, polyesters and the like. The specific material employed must be mutually compatible with the fluids employed in conjunction with balloon 420 and must be able to withstand the pressures that are developed within balloon 420. Balloon wall 422 can have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness can be in the range of about 0.0005 inch to about 0.003 inch, the diameter of balloon 320 in the expanded configuration can be in the range of about 2 millimeters (mm) to about 10 mm, and the length can be in the range of about 3 mm to about 40 mm. The specific specifications, however, may vary depending on the procedure for which balloon 420 is to be used and the anatomy and size of the target lumen in which balloon 420 is to be inserted.

Balloon 420 may be expanded by the introduction of a liquid into inflation cannula 418. In one embodiment, liquids containing therapeutic and/or diagnostic agents may be used to inflate balloon 420. In other embodiments, delivery cannula 416 may have a distal end terminating in balloon 420 and inflation cannula 418 may be removed. In this embodiment, balloon 420 may have micropores. In this aspect, a treatment agent such as those described above may be introduced through a delivery lumen (e.g., inflation cannula 418) to expand the balloon (e.g., balloon 420). The treatment agent will expand balloon 420 at relatively low pressure (e.g., 2-3 atm) and diffuse through the pores to a treatment site, such as glomerular capillaries, within the kidney. In some embodiments, the balloon may be expanded to a dimension which partially occludes artery 402 such that blood continues to flow past balloon 420. Partial occlusion may provide a turbulent blood flow distal to delivery device 400 due to the narrowing of the region through which the blood must pass. Partial occlusion may include from about 60% to about 95% lumen occlusion. In this aspect, the treatment agent may be infused into the turbulent blood flow through the pores or an end of delivery cannula 416 distal to balloon 420 into a turbulent blood flow distal to delivery device 400. In this aspect, a homogenous distribution of the treatment agent within the blood flowing to the kidney is achieved. Still further, since the balloon is inflated, backflow is minimized.

In another embodiment, delivery device 400 may include a perfusion shaft (illustrated with a broken line in FIG. 4) to allow blood to continue to flow to a vessel region distal to balloon 420 when balloon 420 is fully inflated to occlude the vessel lumen. In this embodiment, primary cannula 412 is omitted and guidewire cannula 414 includes holes through portions of a wall of guidewire cannula 414 located proximal and distal to balloon 420. In this aspect, guidewire 410 is positioned proximal to an end of guidewire cannula 414 (e.g., about 10 centimeters from the end), and more specifically proximal to the openings, such that blood is free to flow into holes proximal to balloon 420, through guidewire cannula 414 and out the holes of guidewire cannula 414 distal to balloon 420. In this aspect, although the vessel lumen is completely occluded, blood continues to flow to a region upstream from balloon 420 and a turbulent blood flow is created within this region. In this embodiment, balloon 420 may be a porous balloon such that upon delivery of a treatment agent solution through inflation cannula 418 to inflate balloon 420, the solution diffuses through pores of balloon 420 and into the region of turbulent blood flow. In this aspect, delivery cannula 416 may be omitted. Alternatively, balloon 420 may be nonporous and delivery cannula 416 is used to deliver a treatment agent to the region of turbulent blood flow downstream from balloon 420. Although a substantially round balloon is shown in FIG. 4, it is contemplated that for this embodiment, balloon may have any shape deemed desirable for occluding the lumen of blood vessel 402, for example, conical/square, tapered stepped, and offset.

In one embodiment, balloon 420 is a conventional nonporous balloon. In other embodiments, balloon 420 is a porous material such as PEBAX®, Nylon or polyethylene terephthalate (PET) that has tens or hundreds of micropores around its circumference for treatment agent diffusion. A suitable pore size may range, for example, from about 4 microns to about 400 microns, in some embodiments from about 10 microns to about 100 and in some embodiments from about 8 microns to about 15 microns. Still further, the pore size may have a size of at least four times the diameter of a particle to be delivered. Pores may be created by mechanical means or by laser perforation. Pore distribution along a balloon surface may be inhomogeneous to tailor distribution of treatment agent delivery. Balloon 420 may also be retractable into optional sheath (not shown) to tailor a length of a treatment agent delivery region. In an alternative embodiment, the sheath may have an opening on one side to preferentially deliver a treatment agent to one side of the vessel.

Guidewire cannula 414 extends through balloon 420. Guidewire cannula 414 has a lumen sized to accommodate a guidewire 410. Delivery device 400 may be an over the wire (OTW) configuration wherein guidewire cannula 414 extends from a proximal end (external to a patient during a procedure) to a distal end of delivery device 400. Guidewire cannula 414 may also be used for delivery of a treatment agent as previously described such as an agent having a property to inhibit nephropathy or a formulation including vasoactive agents which enhance binding characteristics to glomerular tissue of the kidney when guidewire 410 is removed with delivery device 400 in place. In such case, separate delivery cannula (i.e., delivery cannula 416) may be unnecessary or a delivery cannula may be used to deliver one treatment agent while guidewire cannula 414 is used to deliver another treatment agent.

In another embodiment, delivery device 400 is a RX-type catheter assembly and only a portion of delivery device 400 (e.g., a distal portion 408 including balloon 420) is advanced over guidewire 410. In a RX-type of catheter assembly, typically, the guidewire cannula/lumen extends from the proximal end of the catheter assembly. The proximal guidewire port is typically spaced a substantial distance from the proximal end of the catheter assembly.

Figure 5:
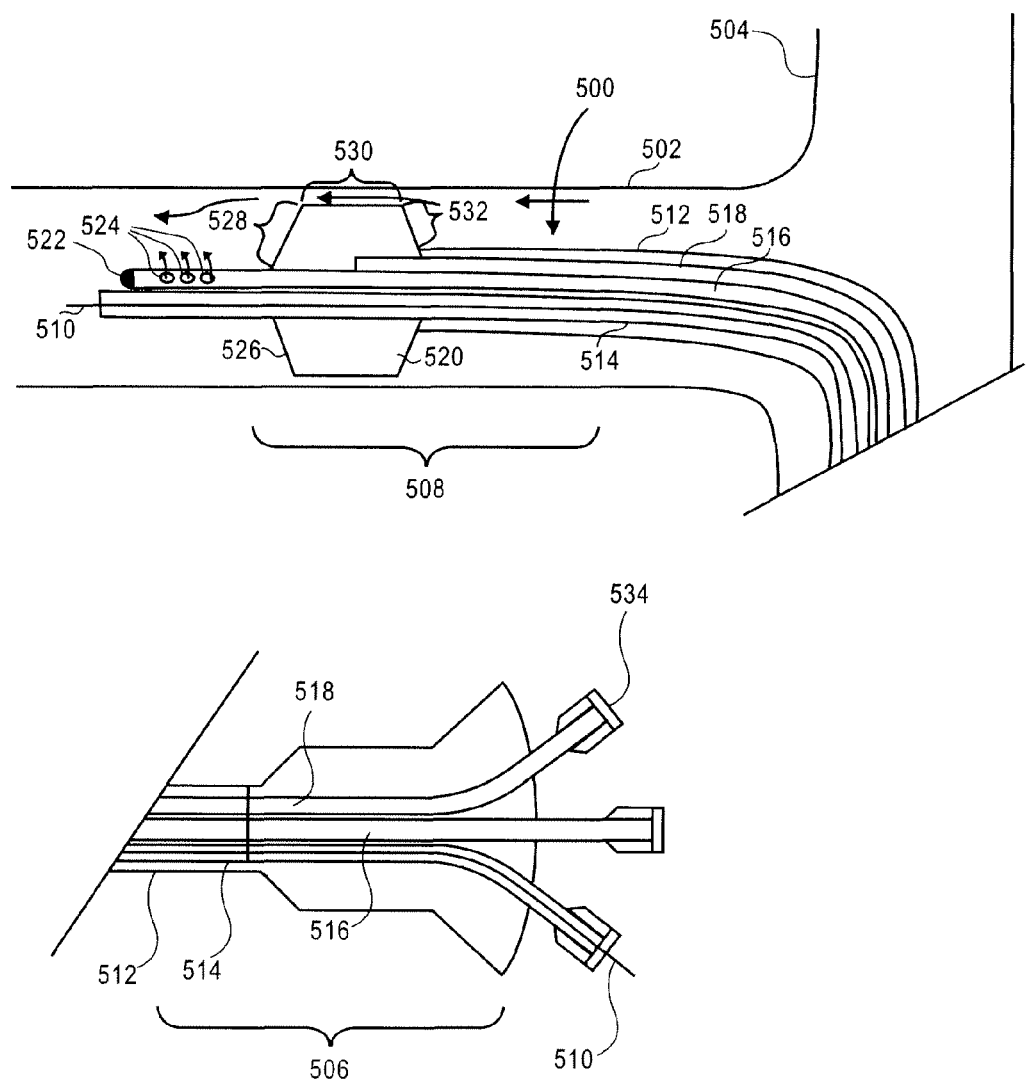
FIG. 5 shows a cross-sectional side view of a blood vessel of a renal region and another embodiment of a delivery system to deliver a treatment to a kidney.

FIG. 5 shows a blood vessel of a renal region and another embodiment of a delivery system to deliver a treatment agent to a kidney. FIG. 5 shows a renal artery 502 branching off of aorta 504 and having a delivery device 500 disposed therein. Delivery device 500 includes a proximal portion 506 and a distal portion 508. Proximal portion 506 may be external to renal artery 502 and to the patient. Representatively, delivery device 500 may be inserted through a femoral artery and through, for example, a guide catheter and with the aid of a guidewire 510 to a location in a renal artery or renal segmental artery of a patient. FIG. 5 shows distal portion 508 of delivery device 500 positioned at a point within renal artery 502. Alternatively, delivery device 500 may be positioned at a point within a renal segmental artery near the renal cortex.

In one embodiment, catheter assembly 500 includes a primary cannula 512 having a length that extends from proximal portion 506 (e.g. located external to a patient during a procedure) to connect with a proximal end or skirt of a balloon 520. Primary cannula 512 has a lumen therethrough that includes a guidewire cannula 514, a delivery cannula 516 and an inflation cannula 518. Primary cannula 514 may be a polymer material that may include markers to allow the cannula to be identified using fluoroscopic or angiographic techniques. For example, a metal band (e.g., stainless steel, platinum, or tungsten loaded polymer) that may be detected by fluoroscopic or angiographic techniques.

Delivery cannula 516 may extend from proximal portion 506 of delivery device 500 to distal portion 508. A distal end of delivery cannula 516 may be occluded 522 so as to prevent fluids from being released out the end. In this aspect, openings 524 may be provided along a length of the distal portion 508 of delivery cannula 516 between balloon 520 and occluded end 522 for delivery of a treatment agent.

Inflation cannula 518 extends from proximal portion 506 of delivery device 500 to distal portion 508. Inflation cannula 518 has a distal end that terminates within balloon 520. Balloon 520 is incorporated at a distal end of delivery device 500 and is in fluid communication with inflation cannula 518. In one embodiment, catheter assembly 500 is introduced into renal artery 502 and balloon 520 is inflated via inflation cannula 518.

Balloon 520 includes balloon wall or membrane 526 which is selectively inflatable to dilate from a collapsed configuration to a desired and controlled expanded configuration. Balloon 520 can be selectively dilated (inflated) by supplying a fluid into inflation cannula 518 at a predetermined rate of pressure through a delivery port 534. Balloon wall 526 is selectively deflatable, after inflation, to return to the collapsed configuration or a deflated profile. In one embodiment, balloon wall 526 can be defined by three sections, distal taper wall 528, medial working length 530, and proximal taper wall 532. In one embodiment, proximal taper wall 528 can taper at any suitable angle θ, typically between about 10° to less than about 90°, when balloon 520 is in the expanded configuration.

Distal taper wall 528, medial working length 530, and proximal taper wall 532 of balloon wall 526 can be bound together by seams or be blown out of a single seamless material. Balloon 520 can be made from any suitable material, including, but not limited to, polymers and copolymers of polyolefins, polyamides, polyesters and the like. The specific material employed must be mutually compatible with the fluids employed in conjunction with balloon 520 and must be able to stand the pressures that are developed within balloon 520. Balloon wall 522 can have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness can be in the range of about 10 microns to about 30 microns, the diameter of balloon 320 in the expanded configuration can be in the range of about 2 millimeters (mm) to about 10 mm, and the length can be in the range of about 3 mm to about 40 mm, the specific specifications depending on the procedure for which balloon 520 is to be used and the anatomy and size of the target lumen in which balloon 520 is to be inserted.

Balloon 520 may be expanded by the introduction of a liquid into inflation cannula 518. In one embodiment, liquids containing a treatment agent may be used to inflate balloon 520. In this embodiment, balloon 520 may have micropores. A treatment agent such as those described above may be introduced through a delivery lumen (e.g., delivery cannula 516 or inflation cannula 518) to expand the balloon (e.g., balloon 520). The treatment agent will expand balloon 520 at relatively low pressure (e.g., 2-3 atm) and diffuse through the pores to a treatment site, such as glomerular capillaries, within the kidney. In this aspect, one or more treatment agents may be delivered through pores of balloon 520 and another through openings 524 of delivery cannula 516. Balloon 520 is inflated to a diameter which partially occludes artery 502 such that blood continues to flow to a region of artery 502 distal to balloon 520. In this aspect, the treatment agent is released from openings 524 or micropores 520 and is delivered to the stream of blood flowing around balloon 520 or distal to balloon 520 in a direction perpendicular to the direction of blood flow. The partial occlusion of the lumen of renal artery 502 and/or delivery of a treatment agent in a direction perpendicular to blood flow create turbulent delivery conditions which facilitate mixing and even distribution of the treatment agent.

In one embodiment, balloon 520 is a conventional nonporous balloon material or a porous material such as PEBAX®, Nylon or PET that has tens or hundreds of micropores around its circumference for treatment agent diffusion. A suitable pore size may range, for example, from about 4 microns to about 400 microns, in some embodiments from about 10 microns to about 100 and in some embodiments from about 8 microns to about 15 microns. Still further, the pore size may have a size of at least four times the diameter of a particle to be delivered. Pores may be created by mechanical means or by laser perforation. Pore distribution along a balloon surface may be inhomogeneous to tailor distribution of treatment agent delivery. Balloon 520 may also be retractable into optional sheath (not shown) to tailor a length of treatment agent delivery. In an alternative embodiment, the sheath may have an opening on one side to preferentially deliver a treatment agent to one side of the vessel.

Guidewire cannula 514 extends through balloon 520. Guidewire cannula 514 has a lumen sized to accommodate a guidewire 510. Delivery device 500 maybe an over the wire (OTW) configuration wherein guidewire cannula 514 extends from a proximal end (external to a patient during a procedure) to a distal end of delivery device 500. Guidewire cannula 514 may also be used for delivery of a treatment agent such as an agent having a property to inhibit nephropathy or a formulation including vasoactive agents which enhance binding characteristics to glomerular tissue of the kidney when guidewire 510 is removed with delivery device 500 in place. In such case, separate delivery cannula (i.e., delivery cannula 516) may be unnecessary or a delivery cannula may be used to deliver one treatment agent while guidewire cannula 514 is used to deliver another treatment agent.

In another embodiment, delivery device 500 is a RX-type catheter assembly and only a portion of delivery device 500 (a distal portion 508 including balloon 520) is advanced over guidewire 510. In a RX-type of catheter assembly, typically, the guidewire cannula/lumen extends from the proximal end of the catheter assembly. The proximal guidewire port is typically spaced a substantial distance from the proximal end of the catheter assembly.

Figure 6:
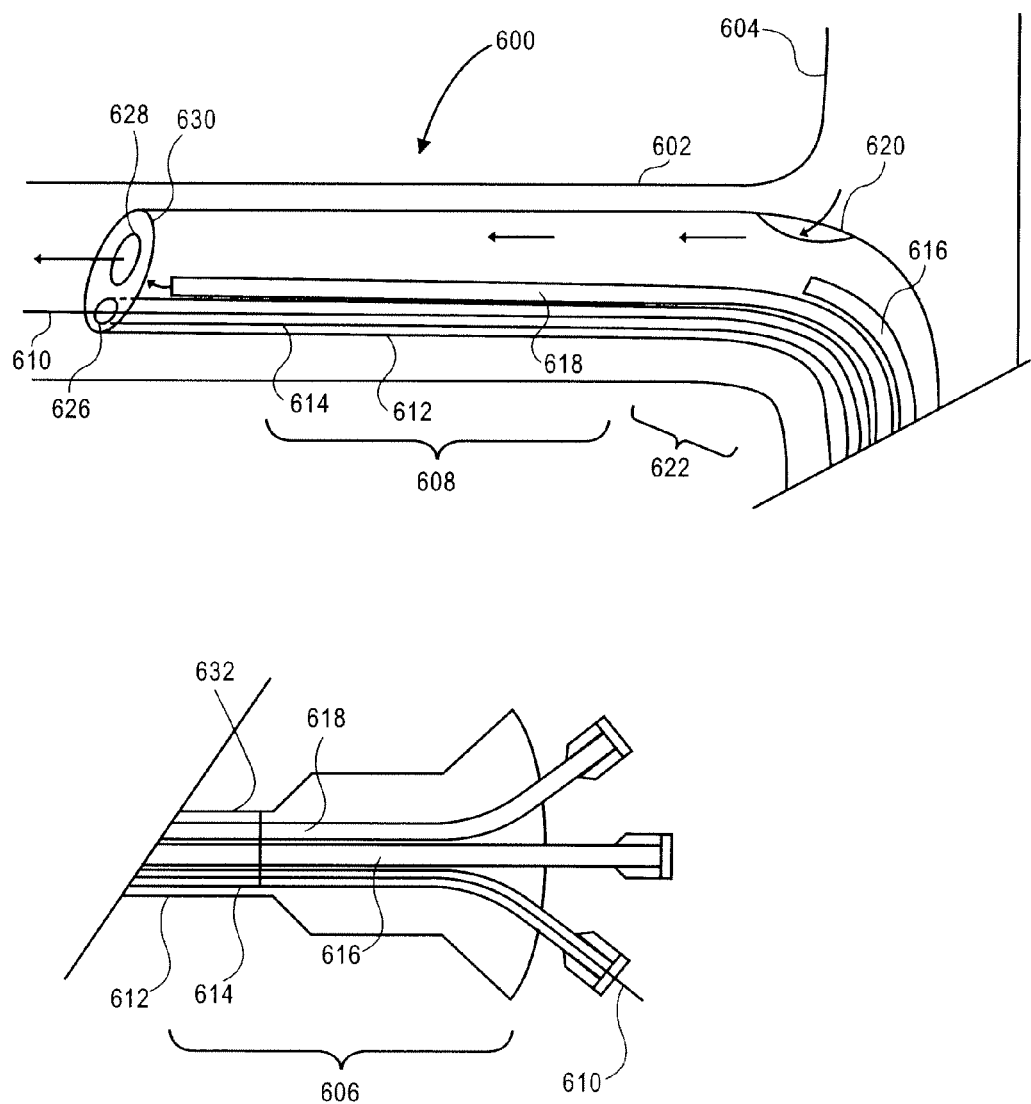
FIG. 6 shows a cross-sectional side view of a blood vessel of a renal region and a perspective view of another embodiment of a delivery system to deliver a treatment agent to a kidney.

FIG. 6 shows a blood vessel of a renal region and another embodiment of a delivery system to deliver a treatment agent to a kidney. FIG. 6 shows a renal artery 602 extending from aorta 604 and having a delivery device 600 disposed therein. Delivery device 600 includes a proximal portion 606 and a distal portion 608. Proximal portion 606 may be external to renal artery 602 and to the patient. Representatively, delivery device 600 may be inserted through a femoral artery and through, for example, a guide catheter and with the aid of a guidewire 614 to a location in a renal artery or renal segmental artery of a patient. In still further embodiments, an external iliac artery may be punctured and delivery device 600 may be advanced through the external iliac artery to a common iliac artery, to aorta 604 and then into renal artery 602. Alternatively, delivery device 600 may be introduced to the point within the renal artery of the patient by inserting delivery device 600 through a region of the patient's back adjacent a kidney and then into the renal artery. In still further embodiments, delivery device 600 may be introduced to a point within a renal cortex of a kidney adjacent glomerular capillaries by inserting delivery device 600 through a region of the patient's back and advancing the delivery device through a region of a retroperitoneal cavity surrounding a kidney into a region of a renal cortex adjacent to glomerular capillaries. FIG. 6 shows distal portion 608 of delivery device 600 positioned at a point within renal artery 602.

In one embodiment, delivery device 600 includes a primary cannula 612 having a length that extends from proximal portion 606 (e.g. located external to a patient during a procedure) to distal portion 608. A medial portion 622 of primary cannula 612 extends between a first end 630 and a second end 632 of primary cannula 612. An aperture 620 may be formed within a wall of primary cannula 612 along medial portion 622. Aperture 620 may be positioned along the wall of primary cannula 612 at a distance from first end 630 of primary cannula 612 such that when first end 630 is positioned within renal artery 602, aperture 620 is positioned within aorta 604. When delivery device 600 is positioned in this manner, aperture 620 is within a stream of blood flowing from aorta 604 and into renal artery 602. In this aspect, blood flowing from aorta 604 to renal artery 602 may be diverted through aperture 620 and into a lumen of primary cannula 612 such that it flows toward first end 630 of primary cannula 612. Aperture 620 may have dimensions suitable to allow a plurality of blood cells to flow therethrough. In one embodiment, aperture 620 is substantially the same size or greater than a size of a first port 628. Representatively, in some embodiments, aperture 620 may have a diameter of from about 0.25 mm to about 3 mm depending upon the diameter of the inner lumen of the catheter or first port 628. It is further contemplated that the diameter of aperture 620 may be adjusted or selected depending on the amount of blood desired to flow therethrough. This diversion of the blood flow into the lumen of primary cannula 612 creates a turbulent blood flow within the lumen. A treatment agent may be released into the turbulent blood flow such that it mixes with the blood to provide a treatment agent and blood solution which flows out first port 628 to the treatment site.

Primary cannula 612 may be a polymer material that may include markers to allow the cannula to be identified using fluoroscopic or angiographic techniques. For example, a metal band (e.g., stainless steel, platinum, or tungsten loaded polymer) that may be detected by fluoroscopic or angiographic techniques.

The lumen of primary cannula 612 includes a guidewire cannula 614, a flush cannula 616 and a delivery cannula 618. First end 630 may include a first port 628 in fluid communication with aperture 620 so that blood flowing into aperture 620 flows through the lumen of primary cannula 612 and out first port 628 to the treatment site. Still further, first port 628 may be in fluid communication with delivery cannula 618 and flush cannula 616. First end 630 may include a second port 626. Second port 626 is dimensioned to receive a guidewire 610 extending through guidewire cannula 614.

Delivery cannula 618 may extend from proximal portion 606 of delivery device 600 to distal portion 608. A distal end of delivery cannula 618 may terminate within distal portion 608 such that a treatment agent delivered from the distal end of delivery cannula 618 is released within the turbulent blood flow created within the lumen of distal portion 608 of primary cannula 612. Alternatively, the distal end of delivery cannula 618 extends through first port 628 such that a treatment agent delivered from delivery cannula 618 is released within the turbulent conditions that may be created within the lumen of renal artery 602.

Flush cannula 616 may extend from proximal portion 606 of delivery device 600 to distal portion 608. Alternatively, flush cannula 616 may be a cannula which terminates within proximal portion 606 of delivery device 600. Blood or another fluid, such as saline, may be loaded into flush cannula 616 at a proximal end of delivery device 600 and infused through the lumen of primary cannula 612 to push or wash out treatment agent and/or blood debris within primary cannula 612. Still further, the delivery of blood and/or other solutions through flush cannula 612 may create a turbulent blood flow either within the lumen of primary cannula 612 or vessel within which delivery device 600 is positioned.

Guidewire cannula 614 has a lumen sized to accommodate a guidewire 610. Delivery device 600 may be an over the wire (OTW) configuration wherein guidewire cannula 614 extends from a proximal end (e.g., external to a patient during a procedure) to a distal end of delivery device 600. Guidewire cannula 614 may also be used for delivery of a treatment agent such as an agent having a property to inhibit nephropathy or a formulation including vasoactive agents which enhance binding characteristics to glomerular tissue of the kidney when guidewire 610 is removed with delivery device 600 in place. In such case, separate delivery cannula (delivery cannula 618) is unnecessary or a delivery cannula may be used to deliver one treatment agent while guidewire cannula 614 is used to deliver another treatment agent.

In another embodiment, catheter assembly 600 is a RX-type catheter assembly and only a portion of catheter assembly 600 (a distal portion 608) is advanced over guidewire 610. In a RX-type of catheter assembly, typically, the guidewire cannula/lumen extends from the proximal end of the catheter assembly. The proximal guidewire port is typically spaced a substantial distance from the proximal end of the catheter assembly.

Figure 7:
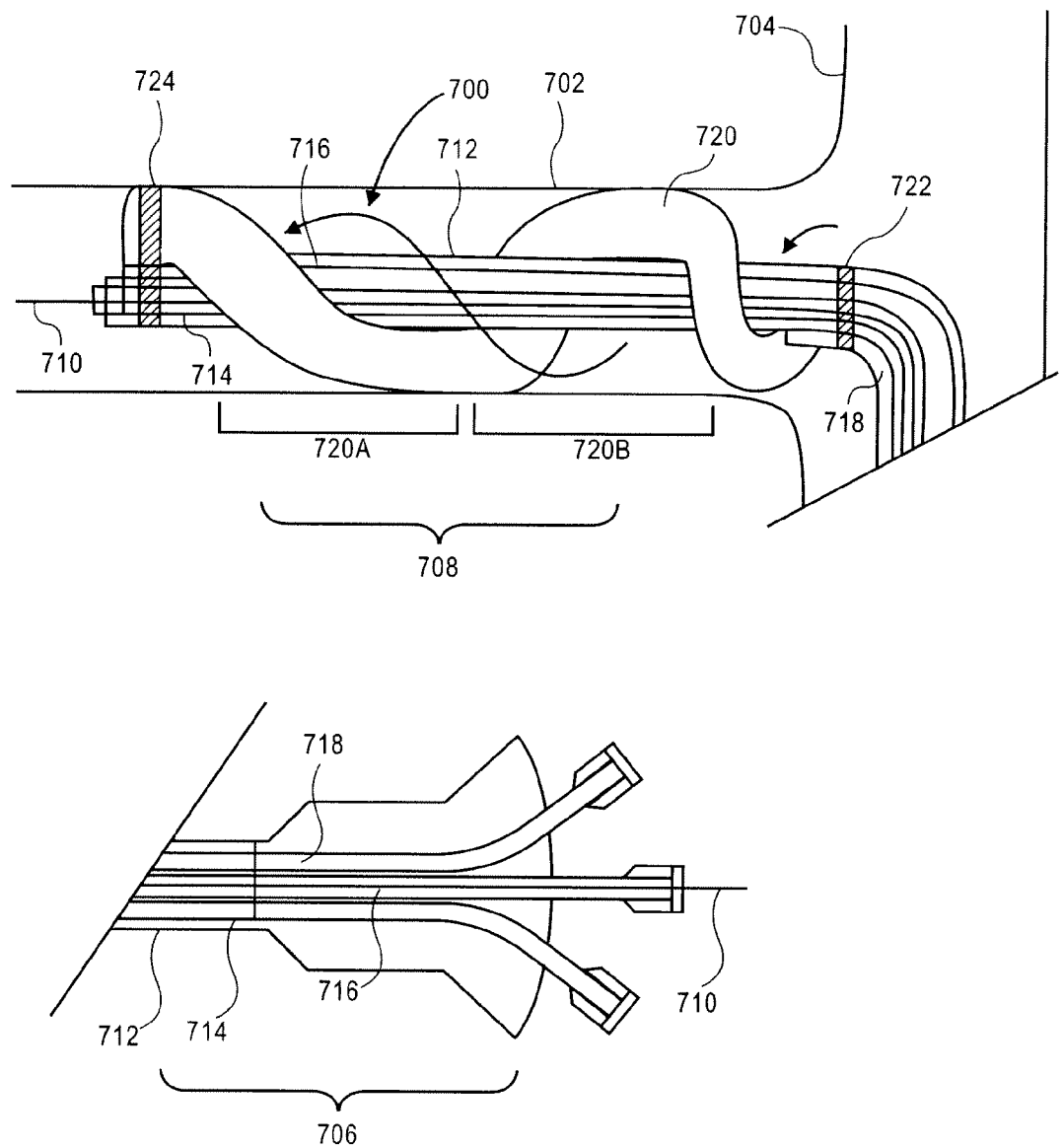
FIG. 7 shows a cross-sectional side view of a blood vessel of a renal region and another embodiment of a delivery system to deliver a treatment agent to a kidney.

FIG. 7 shows a blood vessel of a renal region and another embodiment of a delivery system to deliver a treatment agent to a kidney. FIG. 7 shows a renal artery 702 extending from aorta 704 and having a delivery device 700 disposed therein. Delivery device 700 includes a proximal portion 706 and a distal portion 708. Proximal portion 706 may be external to renal artery 702 and to the patient. Representatively, delivery device 700 may be inserted through a femoral artery and through, for example, a guide catheter and with the aid of a guidewire 714 to a location in a renal artery or renal segmental artery of a patient. FIG. 7 shows distal portion 708 of delivery device 700 positioned at a point within renal artery 702. Alternatively, delivery device 700 may be positioned at a point within a renal segmental artery near the renal cortex.

In this embodiment, delivery device 700 includes primary cannula 712 that has a lumen of a sufficient size to accommodate a guidewire cannula 714 and a delivery cannula 716. In this manner, delivery device 700 may be advanced over guidewire 710 within guidwire cannula 714 to a region of interest or a treatment site. In one embodiment, primary cannula 712 extends from a proximal end of the delivery device intended to be exterior to a patient during a procedure to a distal end of a delivery device. Primary cannula 712 may be a polymer material that may include markers to allow the cannula to be identified using fluoroscopic or angiographic techniques. For example, a metal band (e.g., stainless steel, platinum, or tungsten loaded polymer) that may be detected by fluoroscopic or angiographic techniques.

In the embodiment shown in FIG. 7, delivery device 700 includes an intralumenal framework having a balloon 720 wrapped/spiraled at a distal end around primary cannula 712. In the embodiment shown, balloon 720 includes distal spiral 720A and proximal spiral 720B. Although a distal spiral 720A and proximal spiral 720B are illustrated in FIG. 7, any number of spirals are contemplated. Distal spiral 720A and proximal spiral 720B are connected to primary cannula 712 to anchor device 700 to artery 702 when balloon 720 is expanded. A distal end of inflation cannula 718 positioned along primary cannula 712 terminates within balloon 720 and a proximal end extends to proximal portion 706. In this aspect, a fluid may be delivered through inflation cannula 718 to balloon 720 to expand balloon 720. When balloon 720 is expanded, a corkscrew type channel is formed around primary cannula 712 which allows blood to flow around primary cannula 712 from a region proximal to balloon 720 to a region distal or upstream from delivery device 700. Since the channel is much narrower then the vessel lumen, the flow profile of blood flowing through the channel becomes turbulent resulting in a turbulent blood flow. A treatment agent may then be delivered through delivery cannula 716 which terminates distal to balloon 720 as shown or within distal spiral 720A and released within the turbulent conditions to facilitate even distribution of the treatment agent throughout the kidney.

In one embodiment, balloon 720 may be connected to primary cannula 712 at a distal end by strap 724 and by strap 722 at a portion of primary cannula 712 intended to be positioned proximal to a region of interest. Alternatively, straps 724 and 722 may be omitted and balloon 720 may be bonded to primary cannula 712. In one embodiment, a total inflatable size or length of balloon 720 is on the order of 10 mm to 40 mm. In other embodiments, the total inflatable size or length of balloon 720 is any length less than about 10 mm found suitable to facilitate positioning of delivery device 700 within a renal segmental artery, for example, 8 mm. Representatively, the spacing of adjacent spirals is equivalent to approximately 50 percent of the total inflatable size of the balloon (e.g., from about 5 mm to about 20 mm).

In one embodiment, a material for balloon 720 and its properties are selected so that the balloon expands along its entire length. Suitable materials for balloon 720 include materials that will achieve expansion at inflation pressures on the order of, for example, 6 atm or less. Suitable materials include, but are not limited to, PEBAX® or polytetrafluoroethylene (ePTFE). In another embodiment, only the distal portion of balloon 720 is intended to expand, notably a portion including spiral 720A and spiral 720B. Accordingly, the properties of balloon 720 may be modified along its length making a portion proximal to spiral 720A and spiral 720B resistant to expansion at pressures less than six atmospheres.

In one embodiment, delivery device 700 may be placed at a region of interest using a sheath (not shown) that surrounds primary cannula 712 and balloon 720. In this aspect, a distal portion of primary cannula 712 and balloon 720 may be exposed from the sheath, perhaps by retracting the sheath once delivery device 700 is placed at the region of interest.

The lumen of primary cannula 712 includes guidewire cannula 714 and delivery cannula 716. Delivery cannula 716 may extend from proximal portion 706 of delivery device 700 to distal portion 708. Guidewire cannula 714 has a lumen sized to accommodate a guidewire 710. Delivery device 700 may be an over the wire (OTW) configuration wherein guidewire cannula 714 extends from a proximal end (external to a patient during a procedure) to a distal end of delivery device 700. When guidewire 710 is removed from guidewire cannula 714, guidewire cannula 714 may also be used for delivery of a treatment agent such as an agent having a property to inhibit nephropathy or a formulation including vasoactive agents which enhance binding characteristics to glomerular tissue of the kidney. In such case, a separate delivery cannula (i.e., delivery cannula 716) is unnecessary or delivery cannula 716 may be used to deliver one treatment agent while guidewire cannula 714 is used to deliver another treatment agent.

In another embodiment, catheter assembly 700 is a RX-type catheter assembly and only a portion of catheter assembly 700 (a distal portion 708) is advanced over guidewire 710. In an RX type of catheter assembly, typically, the guidewire cannula/lumen extends from the proximal end of the catheter assembly. The proximal guidewire port is typically spaced a substantial distance from the proximal end of the catheter assembly.

Figure 8:
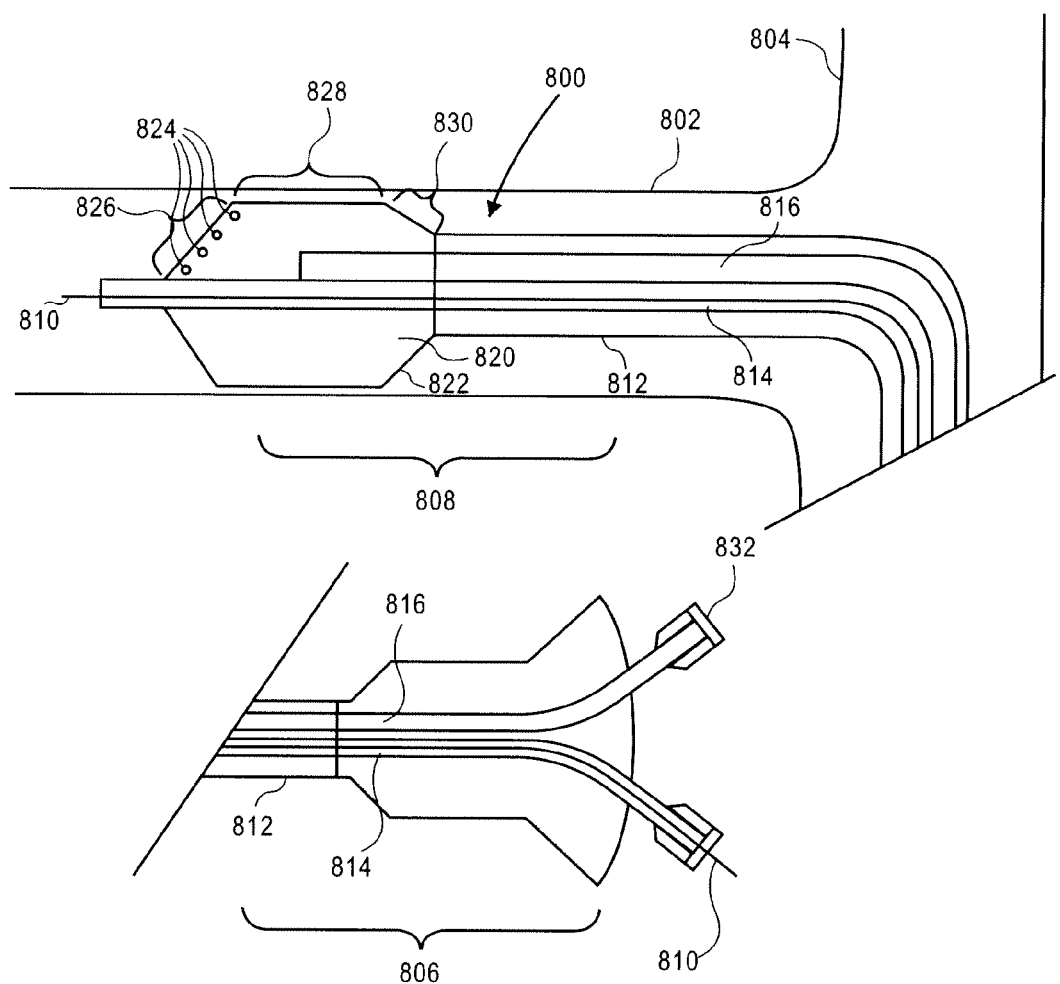
FIG. 8 shows a cross-sectional side view of a blood vessel of a renal region and another embodiment of a delivery system to deliver a treatment agent to a kidney.

FIG. 8 shows a blood vessel of a renal region and another embodiment of a delivery system to deliver a treatment agent to a kidney. FIG. 8 shows a renal artery 802 branching off of aorta 804 and having a delivery device 800 disposed therein. Delivery device 800 includes a proximal portion 806 and a distal portion 808. Proximal portion 806 may be external to renal artery 802 and to the patient. Representatively, delivery device 800 may be inserted through a femoral artery and through, for example, a guide catheter and with the aid of a guidewire 810 to a location in a renal artery or segmental artery of a patient. FIG. 8 shows distal portion 808 of delivery device 800 positioned at a point within renal artery 802.

In one embodiment, delivery device 800 includes a primary cannula 812 having a length that extends from proximal portion 806 (e.g. located external through a patient during a procedure) to connect with a proximal end or skirt of a balloon 820. Primary cannula 812 has a lumen therethrough that includes a guidewire cannula 814 and a delivery cannula 816. Delivery cannula 816 may extend from proximal portion 806 of delivery device 800 to distal portion 808. Delivery cannula 816 has a distal end that terminates within balloon 820. In one embodiment, delivery device 800 is introduced into renal artery 802 and balloon 820 is inflated via delivery cannula 816.

Balloon 820 is incorporated at distal end 808 of delivery device 800 and is in fluid communication with delivery cannula 816. Balloon 820 includes balloon wall or membrane 822 which is selectively inflatable to dilate from a collapsed configuration to a desired and controlled expanded configuration. Balloon 820 can be selectively expanded by supplying a fluid into delivery cannula 816 at a predetermined rate of pressure through a delivery port 832. Balloon wall 822 is selectively deflatable, after inflation, to return to the collapsed configuration or a deflated profile. In one embodiment, balloon wall 822 can be defined by three sections, distal taper wall 826, medial working length 828, and proximal taper wall 830. In one embodiment, proximal taper wall 830 can taper at any suitable angle θ, typically between about 10° to less than about 90°, when balloon 820 is in the expanded configuration.

Distal taper wall 826, medial working length 828, and proximal taper wall 830 of balloon wall 822 can be bound together by seams or be made out of a single seamless material. Balloon 820 can be made from any suitable material, including, but not limited to, polymers and copolymers of polyolefins, polyamides, polyesters and the like. The specific material employed must be mutually compatible with the fluids employed in conjunction with balloon 820 and must be able to stand the pressures that are developed within balloon 820. Balloon wall 822 can have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness can be in the range of about 10 microns to about 30 microns, the diameter of balloon 820 in the expanded configuration can be in the range of about 2 millimeters (mm) to about 10 mm, and the length can be in the range of about 3 mm to about 40 mm, the specific specifications depending on the procedure for which balloon 820 is to be used and the anatomy and size of the target lumen in which balloon 820 is to be inserted.

Balloon 820 may be expanded by the introduction of a liquid into delivery cannula 816. Liquids containing therapeutic and/or diagnostic agents may be used to inflate balloon 820. In one embodiment, balloon 820 may be made of a material that is permeable to such therapeutic and/or diagnostic liquids such as those described above with respect to FIG. 4. To inflate balloon 820, the fluid can be supplied into delivery cannula 816 at a predetermined pressure, for example, from about 1 atm to about 2 atm. Balloon 820 may be expanded to a diameter which partially occludes artery 802 such that blood flowing from aorta 804 may flow past balloon 820 to a vessel region distal to delivery device 800. The blood flow through this region and distal to delivery device 800 is turbulent due to the narrowed region between balloon 820 and the wall of vessel 802 through which the blood must flows. Expansion of balloon 820 as described may further minimize backflow of the treatment agent into the aorta during delivery of the treatment agent to the treatment site.

To facilitate homogenous distribution of the treatment agent throughout the kidney, pores or openings 824 may be provided along distal taper wall 826 of balloon 820. Pores 824 may have any diameter suitable for delivery of a treatment agent therethrough. In one embodiment, the pores may be confined to only a region of distal taper wall 826 defined by a diameter of the lumen of renal artery 802. Any number of pores 824 may be distributed along distal taper wall 826. The treatment agent may be supplied into delivery cannula 816 at the predetermined pressure, and released through pores 824 in multiple directions. The treatment agent then mixes with the turbulent blood flow within this region. Distribution of the treatment agent through pores 824 creates multiple streams of the treatment agent from pores 824. In this aspect, the treatment agent may be distributed more homogenously throughout the blood flowing to the kidney regions.

In one embodiment, balloon 820 is a conventional balloon material such as PEBAX®, Nylon or PET that has tens or hundreds of micropores around its circumference for treatment agent diffusion. A suitable pore size may range, for example, from about 4 microns to about 400 microns, in some embodiments from about 10 microns to about 100 and in some embodiments from about 8 microns to about 15 microns. Still further, the pore size may have a size of at least four times the diameter of a particle to be delivered. Pores may be created by mechanical means or by laser perforation. Pore distribution along a balloon surface may be inhomogeneous to tailor distribution of treatment agent delivery. Balloon 820 may also be retractable into optional sheath (not shown) to tailor a length of treatment agent delivery. In an alternative embodiment, the sheath may have an opening on one side to preferentially deliver a treatment agent to one side of the vessel.

Guidewire cannula 814 extends through balloon 820. Guidewire cannula 814 has a lumen sized to accommodate a guidewire 810. Delivery device 800 may be an over the wire (OTW) configuration wherein guidewire cannula 814 extends from a proximal end (external to a patient during a procedure) to a distal end of delivery device 800. Guidewire cannula 814 may also be used for delivery of a treatment agent such as an agent having a property to inhibit nephropathy or a formulation including vasoactive agents which enhance binding characteristics to glomerular tissue of the kidney when guidewire 810 is removed with delivery device 800 in place. In such case, separate delivery cannula (delivery cannula 816) is unnecessary or delivery cannula 816 may be used to deliver one treatment agent while guidewire cannula 814 is used to deliver another treatment agent.

In another embodiment, delivery device 800 is a RX-type catheter assembly and only a portion of delivery device 800 (a distal portion 808 including balloon 820) is advanced over guidewire 810. In a RX-type of catheter assembly, typically, the guidewire cannula/lumen extends from the proximal end of the catheter assembly. The proximal guidewire port is typically spaced a substantial distance from the proximal end of the catheter assembly.

Figure 9:
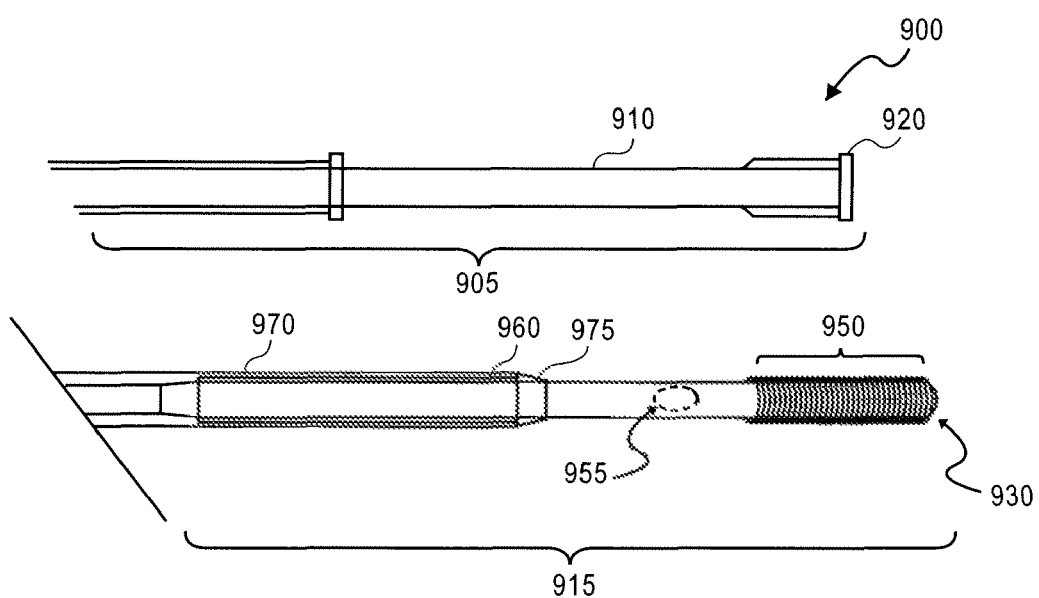
FIG. 9 shows a cross-sectional side view of another embodiment of a delivery system to deliver a treatment agent to a kidney

FIG. 9 shows another embodiment of a delivery system to deliver a treatment agent to a kidney. In this embodiment, delivery device 900 is a hollow guidewire having an assembly for partially occluding and creating turbulence within a vessel lumen. Delivery device 900 includes hollow hypotube body 910 including proximal portion 905 and distal portion 915. Proximal portion 905 is intended to be resident outside of a patient during a procedure while distal portion 915 may be percutaneously inserted, for example, into a femoral or radial artery and advanced to a point within a renal artery and/or a renal segmental artery near a renal cortex for delivery of a treatment agent to a treatment site via a transluminal route (e.g., an arterial route). A suitable treatment site may be diseased glomerular tissue upstream from a renal artery and renal segmental renal artery. Hypotube body 910 of delivery device 900 includes a hollow lumen to allow a treatment agent to be introduced at a proximal port 920 through the lumen of hypotube 910 and exit at distal end 930 of hypotube 910. In one embodiment, hypotube 910 can be made of a metal, like 316L stainless steel, nitinol (NiTi), other metal alloy, or polymer, or combination thereof, with an outer diameter and overall length of the hypotube comparable to most guidewires used for interventional procedures, including, but not limited to, an outer diameter of 0.012 inches, 0.014 inches, 0.018 inches and 0.035 inches. A suitable length includes, but is not limited to, 180 centimeters to 300 centimeters typical of guidewires for rapid exchange and over-the-wire applications, respectively, in interventional procedures.

In one embodiment, delivery device 900 includes a tube or cannula (not shown) extending through the lumen of hypotube 910. The cannula has a lumen therethrough and may be of a flexible polymer material. In this embodiment, a proximal end of the cannula is defined by port 920 to introduce a treatment agent therethrough. A distal end of the cannula extends to distal end 915 of hypotube 910. In this manner, a treatment agent introduced through delivery port 920 is dispersed through a lumen of the cannula and exits delivery device at distal end 930.

In another embodiment, delivery device 910 includes solid tip 950 of a flexible material such as might be used in guidewires in interventional procedures. Such a tip may have a length on the order of up to a few centimeters. In this embodiment, an exit point for a treatment agent such as a treatment agent introduced through the cannula of hypotube 910 may be at a position proximal to tip 950. FIG. 9 shows port 955 (shown in dashed lines) proximal to tip portion 950 (e.g., within 1-2 centimeters from tip portion 950).

Delivery device 900 also includes assembly 960 positioned on hypotube 910. In one embodiment, a distal end of assembly 960 is positioned within a few centimeters of tip 950 (e.g., positioned proximal to an exit point that is proximal to tip 950). In this embodiment, assembly 960 is an expandable cage-like structure that is shown in a collapsed configuration in FIG. 9. FIG. 9 also shows restraining sheath 970 disposed over hypotube 910 from proximal portion 905 to a distal portion beyond assembly 960. Restraining sheath 970 extends co-axially along hypotube 910.

In one embodiment, assembly 960 has an expandable cage that may be deployed by a physician by retracting restraining sheath 970 proximally to expose assembly 960. Once restraining sheath 970 is retracted, the self expanding cage of assembly 960 may immediately begin to expand. In a blood vessel, the assembly will expand until the device contacts a wall of the blood vessel. In one embodiment, delivery device 900 also includes obturator 975 affixed to a distal end of assembly 960. Obturator 975 may be implemented to inhibit possible "snow plowing" of assembly 960 or restraining sheath 970 as it is being delivered through the vasculature.

As noted above, assembly 960, in one embodiment, is an expandable cage-like structure. Suitable cage-like structures are described in the context of embolic filtering devices described in, for example, commonly assigned U.S. Publication No. 2003/0120303, filed Dec. 21, 2001; U.S. Publication No. 2003/0212361, filed Mar. 10, 2003; U.S. Publication No. 2004/0098032, filed Jun. 29, 2001; and U.S. Pat. No. 6,656,202, filed Jun. 29, 2001.

Figure 10:
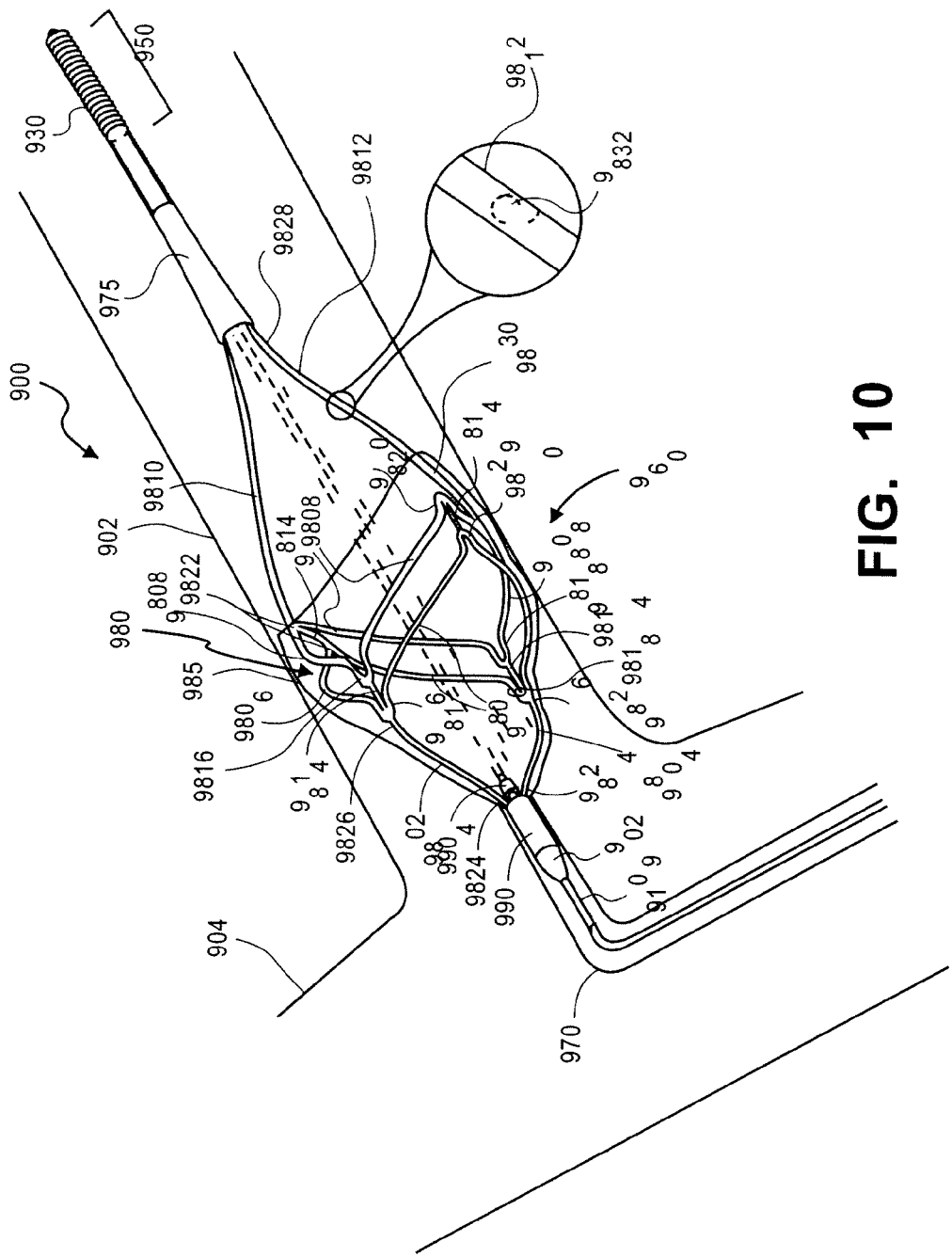
FIG. 10 shows a cross-sectional side view of a blood vessel of a renal region and a top side perspective view of the delivery device of FIG. 9 wherein the delivery device is in an expanded configuration.

FIG. 10 shows a blood vessel of a renal region and a top side perspective view of the delivery device of FIG. 9 wherein the delivery device is in an expanded configuration. Representatively, delivery device 900 is advanced through aorta 904 to renal artery 902 such that assembly 960 is positioned proximal to the kidney. Conventional imaging techniques may be used to position delivery device. In this manner, although not shown, delivery device 900 may include radiopaque markers that are visible under a fluoroscope or other markers (e.g., magnetic resonance imaging markers) to position delivery device 900 at a desired site within a renal artery or segmental artery. Following the positioning of delivery device 900 within the artery, assembly 960 may be deployed as desired. In this embodiment, assembly 960 is deployed by proximally retracting restraining sheath 970 to expose assembly 960 within the blood vessel. In one embodiment, assembly 960 expands immediately upon retraction of restraining sheath 970 without any external aid of force applied to assembly 960. In this aspect, cage structure 980 of assembly 960 may be made of a self expanding material, such as nitinol (NiTi). Assembly 960 expands to an outer diameter of the blood vessel in which delivery device 900 is placed. The wall of a blood vessel may be used to constrain the expansion. It is further contemplated that assembly 960 may be expanded by any suitable technique, for example, with the aid of a balloon assembly.

Assembly 960 may include a sheath 985. Sheath 985 may be of a porous material that permits some blood flow through the porosity and in doing so creates turbulence. In other embodiments, sheath 985 may be selected of a material that inhibits permeation of blood flow past the assembly. In this aspect, assembly 960 when deployed, may partially occlude a blood vessel such that blood may flow around sheath 985 to create a turbulent blood flow. Sheath 985 may only partially envelope an underlying cage structure 980 so as not to completely inhibit blood flow when sheath 985 of a porous material is in an expanded state.

The following description of an embodiment of cage structure 980 is similar to the description of a cage structure for an embolic filtering device described in, for example, commonly assigned U.S. Publication No. 2003/0120303, filed Dec. 21, 2001. It is appreciated that the cage structure presented herein is representative of similar structures described in the referenced application as well as the other applications and patent referenced above.

In one embodiment, cage structure 980 of assembly 960 includes a pair of self-expanding proximal struts 9802 and 9804 that help to deploy assembly 960 and the remainder of the expandable cage. Proximal struts 9802 and 9804 are connected to first circumferential member 9806 which is adapted to move from an unexpanded delivery position to the expanded deployed position. Second circumferential member 9808 is, in turn, connected to first circumferential member 9806. The deployment of first circumferential member 9806 and second circumferential member 9808 results in assembly 960 being placed against a wall of an artery or other blood vessel, even if the lumen of the blood vessel is non-circular. A pair of distal struts 9810 and 9812 connected to second circumferential member 9808 extend distally toward obturator 975. First circumferential member 9806 and second circumferential member 9808 are connected to, and spaced apart, from each other by short connecting struts 9814. It should be appreciated that a single circumferential member could be used to create an expandable cage. Also, additional circumferential members could be added to create a larger expandable cage. Additionally, while two proximal struts and distal struts are shown in the cage design of FIG. 10, the cage could also be made with single proximal and distal struts or additional struts could be implemented.

In one embodiment, each circumferential member includes four bending regions, 9816, 9818, 9820 and 9822 formed on the circumferential member to enhance the performance of the circumferential member to bend as it moves between an unexpanded and an expanded position. Each bending region 9816, 9818, 9820 and 9822 is placed on the circumferential member approximately 90 degrees apart. Each of the proximal struts includes a first end 9824 attached to collar 990 which is rotatably mounted to hypotube 910. Each proximal strut includes second end 9826 connected to one of the proximal bending regions 9816 and 9818 of first circumferential member 9806. This proximal bending regions 9816 and 9818 are spaced approximately 180 degrees apart from each other along a circular diameter defined by circumferential member 9806 in an expanded state. Each of distal struts 9810 and 9812, in turn, have first end 9828 connected to and extending towards obturator 975 and a second end 9830 attached to distal bending regions 9820 and 9822 of second circumferential member 9808. These distal bending regions 9820 and 9822, in turn, are spaced approximately 180 degrees apart from each other and are offset 90 degrees from proximal bending regions 9816 and 9818.

Each of the bending regions is substantially U-shaped which help to create a natural bending point on the circumferential member. While the flexibility of the circumferential member is already high, these bending regions only help to increase the ability of the circumferential member to collapse or expand when needed. In this manner, the shape of the hinge region creates a natural hinge that helps to actuate the expandable cage between an unexpanded and an expanded position. As shown in FIG. 10, U-shaped bending regions 9816 and 9822 are positioned directly opposite the U-shaped portion of bending regions 9818 and 9820. The positioning of the direction of the U portion also enhances the ability of the circumferential member to bend. Circumferential member 9816 and circumferential member 9818, while being bendable, nevertheless may maintain sufficient radial strength to remain in the deployed position to hold assembly 960 open in a blood vessel for occluding blood flow.

The shape of the bending regions are shown as substantially U-shaped portions, however, any one of a number of different shapes could be utilized to create a natural bending point on a circumferential member. For example, a V-shaped region could also be formed and would function similarly to a U-shaped portion to facilitate the collapse and expansion of a circumferential member as needed. Alternative shapes and sizes of the bending regions could also be utilized. Although four bending regions are shown on each circumferential member, it is appreciated that the number of bending regions could be increased or decreased as needed. For example, it is possible to utilize only two bending regions. Additional bending regions also could be utilized in the event that additional proximal or distal struts are used to form the expandable cage. Moreover, different sizes, shapes and location of the bending regions can be utilized on any circumferential member.

In the embodiment shown in FIG. 10, expandable cage structure 980 of assembly 960 is shown rotatably mounted to a distal end of hypotube 910 to allow the entire assembly 960 to remain stationary once deployed in a blood vessel. This feature prevents the assembly from rotating in the event that the proximal end of hypotube 910 is rotated by the physician during use. As a result, the possibility that the deployed assembly can be rotated to cause trauma to a wall of a blood vessel minimized. First end 9824 of proximal struts 9802 and 9804 are attached to collar 990 which is rotatably mounted on hypotube 910 between a pair of stop fittings 9902 and 9904. Stop fittings 9902 and 9904 allow expandable cage structure 980 to spin on hypotube 910 but restrict the longitudinal movement of the cage on the hypotube. A distal end of cage structure 980 may be connected to obturator 975 which may similarly be free to rotate on hypotube 910.

An expandable cage such as shown in detail with reference to FIG. 10 may be made in a variety of ways. One particular method of making cage 980 is to cut a thin-walled tubular member, such as NiTi hypotube, to remove portions of the tubing in a desired pattern for each strut, leaving relatively untouched the portions of the tubing which are to form each strut. The tubing may be cut into the desired pattern by means of a machine-controlled laser. The tubing used to make cage 980 could possibly be made of suitable biocompatible materials such as spring steel. Elgiloy is another material which could possibly be used to manufacture cage 980. Also, certain polymers could be used.

In one embodiment, a strut size is relatively small, so the tubing from which the cage is formed may have a small outside diameter. Typically, the tubing has an outside diameter on the order of from about 0.020 to about 0.100 inches in an unexpanded condition. Also, cage 980 can be cut from large diameter tubing. Fittings are attached to both ends of the lased tube to form the final cage geometry. One suitable wall thickness of tubing is about 0.076 millimeters (about 0.002 inches to about 0.003 inches). As can be appreciated, the strut widths and/or depths at the bending point may be less. Further details of manufacturing a cage such as shown in FIG. 10 may be found with reference to the above-noted applications and patent describing embolic filtering devices.

In still further embodiments, cage 980 may be made from formed tubing with micro-holes that allow agent delivery through the holes. In this aspect, cage 980 may be made from a NiTi hypotube wherein a distal end of the hypotube within renal artery 970 includes perfusion holes 9832 such that a treatment agent delivered to the NiTi hypotube perfuses through holes 9832. In one embodiment, perfusion holes 9832 may be formed along regions of NiTi hypotube cage 980 facing a center of the blood vessel such that when a treatment agent is delivered through holes 9832 and into the blood flowing distal to sheath 985, further turbulence is provided. In this aspect, hypotube 910 may have a distal end terminating within a lumen of NiTi hypotube cage 980 to allow a treatment agent to be introduced at a proximal port 920 through the lumen of hypotube 910 and exit through holes of NiTi hypotube cage 980. In this embodiment, distal end 930 may be eliminated. Alternatively, two hypotubes, one in fluid communication with distal end 930 and the other in fluid communication with NiTi hypotube cage 980 may be provided such that a treatment agent may be delivered from both distal end 930 and perfusion holes of NiTi hypotube cage 980. NiTi hypotube cage 980 may be similar in some respects to the device described in copending U.S. patent application Ser. No. 11/407,707, titled Devices and Methods for Intravascular Drug Delivery, filed on Apr. 19, 2006, incorporated herein by reference.

In some embodiments, cage 980 is composed of a bioabsorbable polymer or biostable polymer. A polymer or coating is "bioabsorable" or "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is "degradable or erodable" when it can be gradually broken down, resorbed, absorbed and eliminated by, for example, hydrolysis, enzymolysis, metabolic processes, bulk or surface erosion, and the like within a mammal. It is to be appreciated that traces of residue of polymer may remain following biodegradation. A "biostable" polymer is a polymer that is not bioabsorbable.

Suitable polymers used in embodiments of a material for cage 980, include, but are not limited to, hydrophobic, hydrophilic, ampiphilic, biodegradable, or a combination thereof. Examples of hydrophobic polymers include, but are not limited to, poly(ester amide), polystyrene-polisobutylene-polystyrene block copolymer (SIS), polystyrene, polyisobutylene, polycaprolactone, poly(L-lactide), poly(D,L-lactide), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hydroxyhexanoate), mid-chain polyhydroxyalkanoate, poly(trimethylene carbonate), poly(orthoester), polyphosphohazene, poly(phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly(vinylidene fluoride-co-hexafluoropropylene (PVDF-HFP), poly(vinylidene fluoride-co-chlorotrifluoroethylene) (PVDF-CTFE), poly(butyl methacrylate), poly(methyl mathacrylate), poly(vinyl alcohol) (PVA), poly(ethylene-co-vinyl acetate), poly(ethylene-co-vinyl alcohol), poly(ester-urethane), poly(ether-urethane), poly(carbonate-urethane), poly(silicone-urethane), poly(2-hydroxyethyl methacrylate), SOLEF® polyvinylidene fluoride (PVDF), poly(urea-urethane), and combinations thereof.

Examples of hydrophilic polymers include, but are not limited to, polymers and co-polymers of hydroxyethly methacrylate (HEMA); poly(methyl methacrylate) (PMMA); poly(ethylene glycol)acrylate (PEGA); PEG methacrylate; phosphorylcholine; 2-methacryloyloxyethyl phosphorylcholine (MPC); n-vinyl pyrrolidone (VP); carboxylic acid bearing monomers such as methacrylic acid (MA), acrylic acid (AA); hydroxyl bearing monomers such as HEMA, hydroxypropyl methacrylate (HPMA), hydroxypropylmethacrylamide, alkoxymethacrylate, alkoxyacrylate, and 3-trimethylsilylpropyl methacrylate (TMSPMA), poly(ethylene glycol) (PEG), poly(propylene glycol) (PPG), SIS-PEG-polystyrene-PEG, polisobutylene-PEG, PCL-PEG, PLA-PEG, PMMA-PEG, PDMS-PEG, PVD-PEG, PLURONIC® surfactants (poly-propylene oxide-co-polyethylene glycol), poly(tetramethylene glycol), hydroxyfunctinal poly(vinyl pyrrolidone), polyalkylene oxide, dextran, detrin, sodium hyaluronate, hyaluronic acid, heparin, elastin, chitosan; and combinations thereof.

Examples of biodegradable polymers include, but are not limited to, polymers having repeating units such as, for example, an α-hydroxycarboxylic acid, a cyclic diester of an α-hydroxycarboxylic, a dioxanone, a lactone, a cyclic carbonate, a cyclic oxalate, an epoxide, a glycol, an anhydride, a lactic acid, a glycolic acid, a clycolic acid, a lactide, a glycolide, an ethylene oxide, an ethylene glycol, or combinations thereof.

In some embodiments, the biodegradable polymers include, but are not limited, to polyesters, polyhydroxyalkanoates (PHAs), poly(ester amides), amino acids, PEG and/or alcohol groups, polycaprolactones, poly(L-lactide), poly(D,L-lactide, poly(D,L-lactide-co-PEG) block copolymers, poly(D,L-lactide-co-trimethylene carbonate), polyglycolides, poly(lactide-co-glycolide), polydioxanones, polyorthoesters, polyahydrides, poly(glycolic acid-co-trimethylene carbonate), polyphosphoesters, polyphosphoester urethans, poly(amino acids), polycyanoacrylates, poly(trimethylene carbonate), poly(imino carbonate), polycarbonates, polyurethanes, copoly(ether-esters) (e.g., PEO/PLA), polyakylene oxalates, polyphosphazenes, PHA-PEG, and any derivatives, analogs, homologues, salts, copolymers and combinations thereof.

A composition including a treatment agent (or multiple treatment agents) and a stimuli-responsive polymer may be included in a cage coating on cage 980 or included in the body of cage 980 such as, for example, a biodegradable polymeric cage. The release profile of the particles of treatment agent and polymer can be controlled by tailoring the chemical composition and crystallinity of the polymer as the coating or the bioabsorbable stent material (e.g., the more crystalline the slower the release rate).

In the embodiment described, expandable cage structure 980 is covered by sheath 985. Sheath 985 may be of a porous material, such as, but not limited to PEBAX®, Nylon or PET that has tens or hundreds of micropores around its circumference for treatment agent diffusion. Alternatively, pores of a desired dimension may be formed in a suitable material by mechanical means or by laser perforation. In still further embodiments, sheath 985 may be a polymeric material such as, but not limited to, polyurethane or GORTEX®, a commercially available material. Other suitable materials include expanded ePTFE. The material may be elastic or non-elastic. A suitable wall thickness of sheath 985 can be about 0.0005-0.005 inches. The wall thickness may vary depending on the particular material selected. The material can be made into a cone or similarly size shape utilizing blow-mold technology or dip technology. Additionally, a material for sheath 985 can have a "set" put in a much like the set used in a dilation balloon to make the sheet rewrap more easily when placed in a collapsed position.

A suitable material for restraining sheath 970 can be polymer material such as cross-linked high density polyethylene (HDPE). Restraining sheath 970 can alternatively be made from a material such as a polyolefin that has sufficient strength to hold the compressed assembly 960 and has relatively low frictional characteristics to minimize any friction between the occlusion device and the sheath. Friction can be further reduced by applying a coat of silicone lubricant, such as MICROGLIDE®, to the inside surface of the restraining sheath before the sheath is placed over assembly 960.

Figure 11:
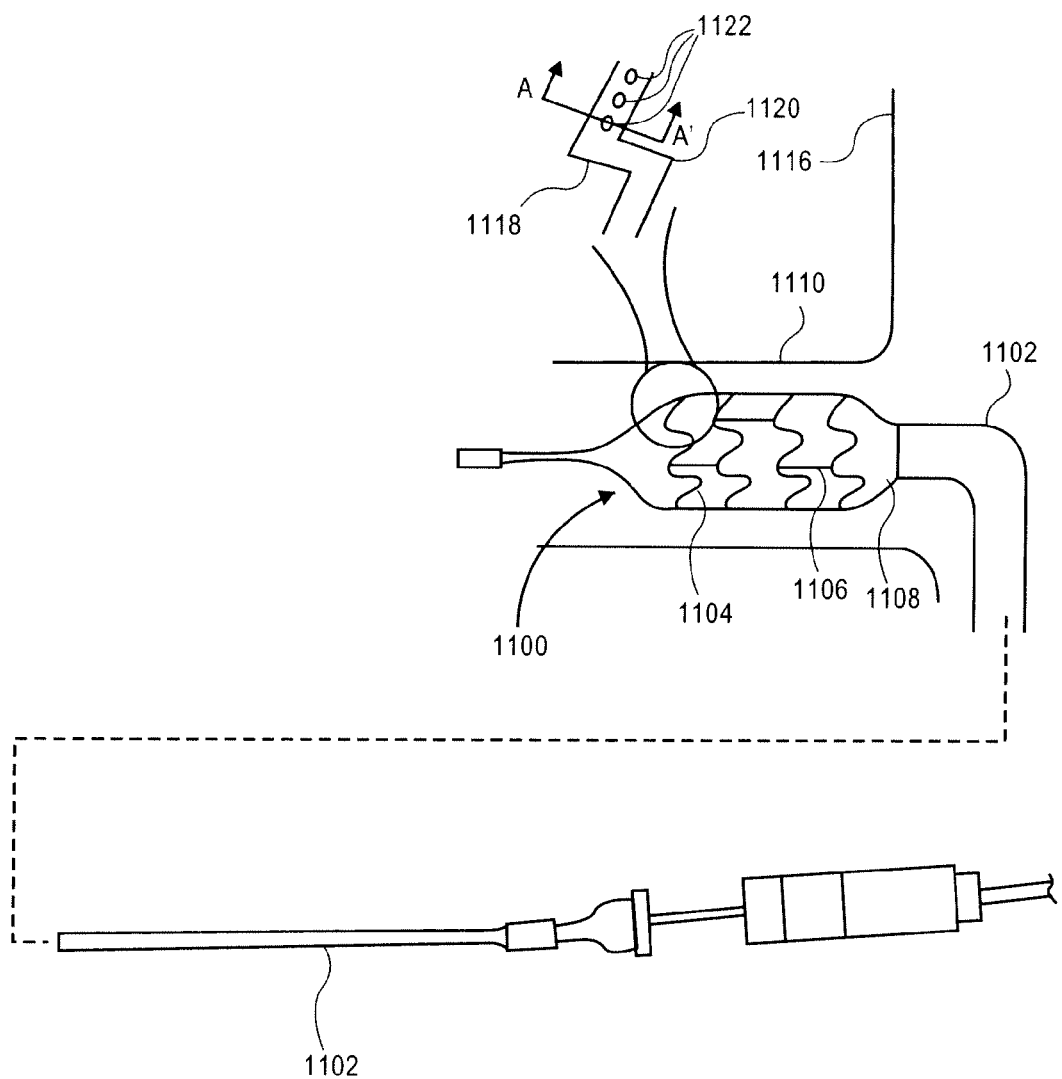
FIG. 11 shows a cross-sectional side view of another embodiment of a delivery system to deliver a treatment agent to a kidney.

FIG. 11 shows another embodiment of a delivery system to deliver a treatment agent to a kidney. FIG. 11 shows a renal artery 1110 extending from aorta 1116 and having a delivery device 1100 disposed therein. Delivery device 1100 is similar in some respects, for example, to commonly owned U.S. application Ser. No. 10/802,435, titled Stent Deployable at a Low Pressure and a Stent Delivery System, filed on Mar. 16, 2004.

In this embodiment, the delivery device is a stent implant 1100. Stent implant 1100 is mounted onto a delivery catheter 1102. In one embodiment, stent 1100 is mounted on a distal portion of delivery catheter 1102. Stent 1100 includes a plurality of radially expandable cylindrical elements (a plurality of struts) 1104 disposed generally coaxially and interconnected by connecting elements (a plurality of links) 1106 disposed between adjacent struts 1104. The delivery catheter 1102 has an expandable portion or a balloon 1108 for expanding of stent 1100 within renal artery 1110. Stent 1100 is configured so that it can be deployed within renal artery 1110 at a low pressure so as to reduce injury and/or trauma to the vessel. For example, stent 1100 may be deployed at lower than 6 atm, in some embodiments, lower than about 3 atm, and in some other embodiments, even lower than about 1 atm. One approach for stent 1100 to be deployed at a substantially low pressure (e.g., ≦6 atm, ≦3 atm, and ideally, ≦1 atm) is to configure stent 1100 with substantially narrow struts 1104. In this aspect, struts 1104 of stent 1100 may be in the range of about 0.0018 inches to about 0.025 inches. Narrower struts 1104 allow stent 1100 to deploy at low pressure. In one embodiment, stent 1100 has a tubular shape. When stent 1100 is expanded, its diameter (tubular diameter) expands as bar arm portions 1118 and crown portions 1120 straighten due to the pressure that is applied to expand stent 1100.

It is within the scope and contemplation of the present invention that strut 1104 widths and lengths can be varied in conjunction with the different materials used to make stent 1100 able to deploy. For instance, when a stiffer material is used to makes stent 1100, stent 1100 is configured to be thinner and longer than when a less stiff material is used. Materials that may be used to make stent implant 1100 include, but are not limited to, cobalt chromium (CoCr) alloy, cobalt alloy, nickel alloy, tantanum alloy, nickel titanium alloy, stainless steel, or other corrosion resistant alloy or a biodegradable material. Still further, stent 1100 may be made of a polymer material such that a treatment agent may be embedded in a matrix of the polymer material. In some embodiments, stent 1100 may be coated with a permeabilizing reagent for increasing the permeability of membrane junctions or cell membranes. Suitable permeabilizing agents may include ethylene vinyl alcohol copolymer (commonly known by the generic name EVOH or by the trade name EVAL®), poly(hydroxyvalerate); poly(L-lactic acid); polycaprolactone to name a few. In some embodiments, stent 1100 is composed of a bioabsorbable polymer or biostable polymer similar to that described above in regard to cage 980 of FIG. 9.

As illustrated in the exploded view of strut 1104, each of struts 1104 further include bar arm portions 1118 and crown portions 1120. Depots 1122 are provided in struts 1104 for carrying and release of a treatment agent. An opening of each depot 1122 may be positioned on a side of strut 1104 adjacent a flow of blood along a lumen of renal artery 1110 such that the treatment agent is released in the direction of the artery lumen as opposed to a wall of the artery. Various embodiments of depots 1122 of stent 1100 will be described in more detail with reference to FIGS. 12-14.

Figure 12:
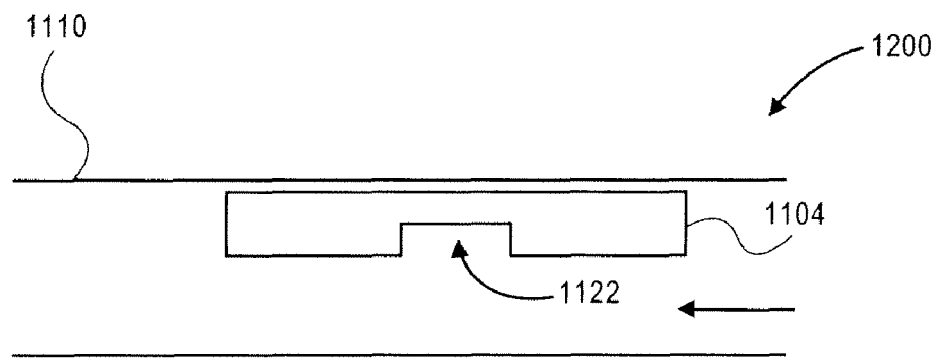
FIG. 12 shows a cross-sectional side view through line A-A' of one embodiment of a strut of the stent delivery system of FIG. 11.
Figure 13:
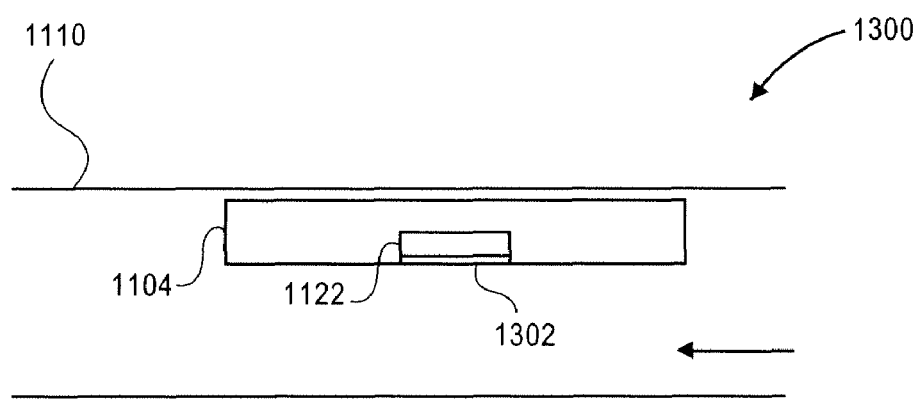
FIG. 13 shows a cross-sectional side view through line A-A' of another embodiment of a strut of the stent delivery system of FIG. 11.

FIG. 12 shows a cross-sectional side view through line A-A' of one embodiment of a strut of the stent delivery system of FIG. 11. In this embodiment, a cross section along A-A' of depot 1122 of delivery device 1200 is shown having a depth less than the thickness of the wall of strut 1104. In this aspect, depot 1122 has a single opening positioned along a lumen of renal artery 1100. FIG. 13 shows a cross-sectional side view through line A-A' of another embodiment of a strut of the stent delivery system of FIG. 11. In this embodiment, a cross section along A-A' of depot 1122 of delivery device 1300 is shown. Similar to the depot of FIG. 12, the depth of depot 1122 of delivery device 1300 is less than the thickness of the wall of strut 1104. In some embodiments, depot 1122 may have a rectangular dimension of from about 0.002 inches to about 0.005 inches in width and about 0.002 inches to about 0.100 inches in length. The depot can also be a round depot and have a diameter of from about 0.002 inches to about 0.006 inches. Depot 1122, may have a depth of from about 0.002 inches to about 0.005 inches. A membrane 1302 extends across the opening of depot 1122 to modify a release rate of a treatment agent loaded within depot 1122. The treatment agent may be loaded within depot 1122 through the opening of depot 1122 and then membrane 1302 placed over the opening prior to insertion of the delivery device into the vessel. Membrane 1302 may be a polymer material. In one embodiment, a material of membrane 1302 may include, but is not limited to, a hydrophilic polymer such as PVA. Still further, the material of membrane 1302 may be a cross-linked PVA to modify a rate of release of the treatment agent eluted from depot 1122. It is further contemplated that the specifications of membrane 1302, for example, a thickness, may be modified to achieve a desired release rate. Alternatively, membrane 1302 may be coated with any material having a property to modify a release rate.

Figure 14:
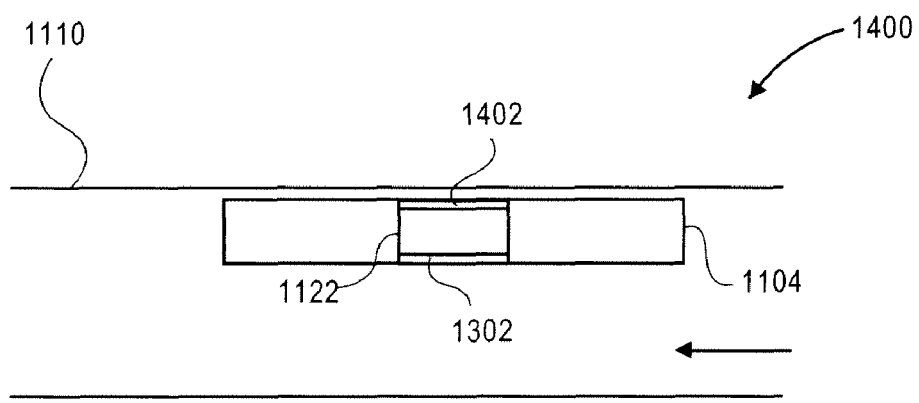
FIG. 14 shows a cross-sectional side view through line A-A' of another embodiment of a strut of the stent delivery system of FIG. 11.

FIG. 14 shows a cross-sectional side view through line A-A' of another embodiment of a strut of the stent delivery system of FIG. 11. In this embodiment, a cross section along A-A' of depot 1122 of delivery device 1400 is shown. In this embodiment, depot 1122 of delivery device 1400 has a depth substantially equivalent to the thickness of strut 1104 such that depot 1122 has an opening on each side of strut 1104. The greater depth of depot 1122 allows a greater amount of the treatment agent to be loaded into depot 1122 for delivery. It is further contemplated that a diameter of depot 1122 may be altered to increase the space within depot 1122 within which the treatment agent is loaded. A film or cap 1402 is provided along an opening of depot 1122 adjacent the wall of renal artery 1110. Membrane 1302 similar to that described in reference to FIG. 13, may be positioned across an opening of depot 1122 opposite to the opening cap 1402 is placed over. In this aspect, the treatment agent may be loaded in one of the openings of depot 1122 and retained within depot 1122 by cap 1402 and membrane 1302. Alternatively, depot 1122 may include only cap 1402 adjacent a wall of vessel 1110 such that a treatment agent loaded into depot 1122 is released into the flow of blood instead of the wall of renal artery 1110. Cap 1402 may be made of any material suitable for sealing the opening and retaining the treatment agent. The specific material employed must be mutually compatible with the fluids employed in conjunction with depot 1122. Representatively, the material suitable for cap 1402 may include, but is not limited to, polymers and copolymers of polyolefins, polyamides, polyesters and the like.

In the preceding detailed description, specific embodiments are illustrated, including a variety of devices and method for delivering a treatment agent to a kidney region according to conditions which create a turbulent blood flow within a region of agent delivery. It will, however, be evident that various modifications and changes may be made thereto without departing from the broader spirit and scope of the invention as set forth in the claims. For example, the devices are described for delivering a treatment agent to a kidney region. It is contemplated that, the devices and method may be suitable for delivering a treatment agent to a treatment site within any blood vessel or organ of the body. The specification and drawings are, accordingly, to be regarded in an illustrative rather than a restrictive sense.

What is claimed is:

1. A method comprising:
    introducing a delivery device to a point within a renal artery, the delivery device comprising a primary cannula having a first end, a second end and a medial region between the first end and the second end, wherein the first end comprises a first port and a second port, the medial region comprises at least one longitudinally disposed aperture in fluid communication with the first port such that blood flowing toward the renal artery flows into the primary cannula through the aperture and out the first port to the renal artery, and the second port is adapted for advancing a guidewire there through; and
    delivering a treatment agent along with the blood flowing through the primary cannula from the first port to create a turbulent blood flow into the kidney in addition to any turbulent conditions from the presence of the delivery device in the renal artery, wherein said treatment agent is capable of inhibiting a biological process contributing to nephropathy.

2. The method of claim 1 wherein the first end of the delivery device is positioned within the renal artery and the aperture is positioned within an aorta such that the blood flowing from the aorta is diverted through the aperture and into the primary cannula.

3. The method of claim 1 wherein the treatment agent is mixed with the blood flowing through the primary cannula prior to delivering the treatment agent from the first port.

* * * * *